US008652481B2

(12) United States Patent
Beck et al.

(10) Patent No.: US 8,652,481 B2
(45) Date of Patent: Feb. 18, 2014

(54) *MYCOPLASMA BOVIS* VACCINE AND METHODS OF USE THEREOF

(75) Inventors: Michael Beck, St. Joseph, MO (US); Jeffrey Knittel, St. Joseph, MO (US)

(73) Assignee: Boehringer Ingelheim Vetmedica, Inc., St. Joseph, MO (US)

( * ) Notice: Subject to any disclaimer, the term of this patent is extended or adjusted under 35 U.S.C. 154(b) by 947 days.

(21) Appl. No.: 12/260,520

(22) Filed: Oct. 29, 2008

(65) Prior Publication Data

US 2009/0130148 A1 May 21, 2009

Related U.S. Application Data

(60) Provisional application No. 60/983,482, filed on Oct. 29, 2007, provisional application No. 61/075,552, filed on Jun. 25, 2008.

(51) Int. Cl.
*A61K 39/00* (2006.01)
*A61K 39/02* (2006.01)
*A61K 45/00* (2006.01)
*C12N 1/00* (2006.01)

(52) U.S. Cl.
USPC .................. 424/184.1; 424/264.1; 424/278.1; 424/282.1; 435/243

(58) Field of Classification Search
None
See application file for complete search history.

(56) References Cited

U.S. PATENT DOCUMENTS

| 6,548,069 | B2 * | 4/2003 | Hymas et al. ............... 424/201.1 |
| 7,429,389 | B2 | 9/2008 | Leonard et al. | |
| 2002/0150593 | A1 | 10/2002 | Hymas et al. | |
| 2003/0064079 | A1 | 4/2003 | Goudie et al. | |
| 2003/0147914 | A1 * | 8/2003 | Keich et al. ............... 424/201.1 |
| 2003/0180219 | A1 | 9/2003 | Keich et al. | |
| 2005/0053627 | A1 | 3/2005 | Leonard et al. | |
| 2007/0077260 | A1 | 4/2007 | Leonard et al. | |
| 2008/0069842 | A9 | 3/2008 | Leonard et al. | |
| 2008/0193463 | A1 | 8/2008 | Frey et al. | |
| 2008/0226671 | A1 | 9/2008 | Leonard et al. | |
| 2009/0068231 | A1 * | 3/2009 | Kumar et al. ............... 424/264.1 |
| 2009/0130148 | A1 | 5/2009 | Beck et al. | |
| 2010/0272759 | A1 | 10/2010 | Beck et al. | |
| 2011/0059437 | A1 | 3/2011 | Beck | |
| 2012/0093854 | A1 | 4/2012 | Beck et al. | |

FOREIGN PATENT DOCUMENTS

| WO | 9902670 | A1 | 1/1999 |
| WO | 9964604 | A2 | 12/1999 |
| WO | 0134189 | A2 | 5/2001 |
| WO | WO 01/34189 | A2 * | 5/2001 |
| WO | 03004051 | A2 | 1/2003 |
| WO | 03004052 | A1 | 1/2003 |
| WO | 03017755 | A2 | 3/2003 |
| WO | 2005111201 | A1 | 11/2005 |
| WO | 2008030619 | A2 | 3/2008 |
| WO | 2009036241 | A1 | 3/2009 |
| WO | 2009058833 | A2 | 5/2009 |
| WO | 2010002537 | A1 | 1/2010 |
| WO | 2010051210 | A1 | 5/2010 |
| WO | 2010124154 | A1 | 10/2010 |

OTHER PUBLICATIONS

Mostowy et al., "The in vitro evolution of BCG vaccines". 2003, Vaccine, vol. 21, pp. 4270-4274.
Rosengarten et al. "Antigen Heterogeneity among Isolates of *Mycoplasma bovis* Is Generated by High-Frequency Variation of Diverse Membrane Surface Proteins". Nov. 1994, Infection and Immunity, vol. 62, No. 11, pp. 5066-5074.
Thorns, et al., "Effect of Serial Passages Through Liquid Medium on the Virulence of *Mycoplasma-bovis* for the Mouse Mammary Gland", Research in Veterinary Science, vol. 29, No. 3, 1980 pp. 328-332.
Chima et al., "Immunoprophylaxis of Experimental *Mycoplasma bovis* Arthritis in Calves. Protective Efficacy of Live Organisms and Formalinized Vaccines". 1980, Veterinary Microbiology, vol. 5, pp. 113-122.
International Search Report for PCT/US2008/81545 mailed Apr. 15, 2009.
International Search Report for PCT/US2009/061610 mailed Jan. 15, 2010.
Gagea et al., "Naturally occurring *Mycoplasma bovis*-associated pneumonia and polyarthritis in feedlot beef calves". 2006, Journal of Veterinary Diagnostic Investigation, vol. 18, pp. 29-40.
Cai et al., "Development of a real-time PCR for detection of *Mycoplasma bovis* in bovine milk and lung samples". 2005, Journal of Veterinary Diagnostic Investigation, vol. 17, pp. 537-545.
Devriese et al., "Antibiotic Susceptibility Testing of *Mycoplasma bovis* using Tween 80 Hydrolysis as an Indicator of Growth". 1991, Journal of Veterinary Medicine B, vol. 38, pp. 781-783.
Angen et al., "Respiratory disease in calves: Microbiological investigations on trans-tracheally aspirated bronchoalveolar fluid and acute phase protein response". 2009, Veterinary Microbiology, vol. 137, pp. 165-171.
Nicholas et al., "Vaccines for Mycoplasma Diseases in Animals and Man". 2009, Journal of Comparative Pathology, vol. 140, pp. 85-96.
Sachse et al., "Comparison of *Mycoplasma bovis* Strains Based on SDS-PAGE and Immunoblot Protein Patterns". 1992, Journal of Veterinary Medicine B, vol. 39, pp. 246-252.
Nicholas et al., "*Mycoplasmas* in Adult Cattle: Bugs Worth Bothering with?". 2005, British Cattle Veterinary Association, vol. 13, Part 2, pp. 167-170.
Butler et al., "Pasteurization of Discard *Mycoplasma* Mastitic Milk Used to Feed Calves: Thermal Effects on Various *Mycoplasma*". 2000, Journal of Dairy Science, vol. 83, pp. 2285-2288.
Maunsell et al., "*Mycoplasa bovis* Infections in Young Calves". 2009, Vet Clin Food Anim, vol. 25, pp. 139-177.

(Continued)

Primary Examiner — Vanessa L. Ford
Assistant Examiner — Lakia Tongue
(74) *Attorney, Agent, or Firm* — Michael P. Morris; Joyce L. Morrison

(57) ABSTRACT

The present invention relates to new attenuated *M. bovis* bacteria strains. Moreover, the present invention also provides immunogenic compositions comprising live bacteria of an of those attenuated *M. bovis* bacteria strain, their manufacture and use for the treatment and prophylaxis of *M. bovis* infections.

23 Claims, 5 Drawing Sheets

(56) References Cited

OTHER PUBLICATIONS

Khan et al., "Biochemical characterisation of some non fermenting, non arginine hydrolysing *mycoplasmas* of ruminants". 2005, Veterinary Microbiology, vol. 109, pp. 129-134.
Miles et al., "Insertion sequence profiling of UK *Mycoplasma bovis* field isolates". 2005, Veterinary Microbiology, vol. 107, pp. 301-306.
Lin et al., "A rapid chromogenic microtitre assay of arginine aminopeptidase activity in *Mycoplasma* strains". 2006, Systematic and Applied Microbiology, vol. 29, pp. 589-592.
Tenk et al., "Detection of *Mycoplasma bovis* with an Improved PCR Assay". 2006, Acta Veterinaria Hungarica, vol. 54(4), pp. 427-435.
Geary et al., "Inflammatory Toxin from *Mycoplasma bovis*: Isolation and Characterization". May 1981, Science, vol. 212, pp. 1032-1033.
Howard et al., Comparative Pathogenicity of *Mycoplasma bovis* and *Mycoplasma Dispar* for the Respiratory Tract of Calves. 1987, Israel Journal of Medical Sciences, vol. 23, pp. 621-624.
Hannan et al., "Comparative Susceptibilities of Various Animal-Pathogenic Mycoplasmas to Fluoroquinolones". 1997, Antimicrobial Agents and Chemotherapy, vol. 41, No. 9, pp. 2037-2040.
Krysak, D., Chronic pneumonia and polyarthritis syndrome in a feedlot calf. Oct. 2006, Canadian Veterinary Journal, vol. 47, pp. 1019-1022.
Nicholas et al., "An experimental vaccine for calf pneumonia caused by *Mycoplasma bovis*: clinical, cultural, serological and pathological findings". 2002, Vaccine, vol. 20, pp. 3569-3575.
Rosenbusch et al., "In vitro antimicrobial inhibition profiles of *Mycoplasma bovis* isolates recovered from various regions of the United States from 2002 to 2003". 2005, Journal of Veterinary Diagnostic Investigation, vol. 17, pp. 436-441.
Vicca et al., "In Vitro Susceptibilities of *Mycoplasma hyopneumoniae* Field Isolates". Nov. 2004, Antimicrobial Agents and Chemotherapy, vol. 48, No. 11, pp. 4470-4472.
Hannan, P., "Guidelines and recommendations for antimicrobial minimum inhibitory concentration (MIC) testing against veterinary *Mycoplasma* species". 2000, Veterinary Research, vol. 31, pp. 373-395.
Razin et al., "Molecular Biology and Pathogenicity of *Mycoplasmas*". Dec. 1998, Microbiology and Molecular Biology Reviews, vol. 62, No. 4, pp. 1094-1156.
Lysnyansky et al., "Juxtaposition of an Active Promoter to vsp Genes via Site-Specific DNA Inversions Generates Antigenic Variation in *Mycoplasma bovis*". Oct. 2001, Journal of Bacteriology, vol. 183, No. 19, pp. 5698-5708.
Caswell et al., "*Mycoplasma bovis* pneumonia in cattle". 2008, Animal Health Research Reviews, vol. 8(2), pp. 161-186.
Brank et al., "Development of a Recombinant Antigen for Antibody-Based Diagnosis of *Mycoplasma bovis* Infection in Cattle". Nov. 1999, Clinical and Diagnostic Laboratory Immunology, vol. 6, No. 6, pp. 861-867.
Khodakaram-Tafti et al., "Immunohistopathological Findings in the Lungs of Calves Naturally Infected with *Mycoplasma bovis*". 2004, Journal of Veterinary Medicine A, vol. 51, pp. 10-14.
Duarte et al., "Otitis in Cattle, an Aetiological Review". 2004, Journal of Veterinary Medicine B, vol. 51, pp. 1-7.
Bush et al., "Characterization of a lympho-inhibitory peptide produced by *Mycoplasma bovis*". 2004, Biochemical and Biophysical Research Communications, vol. 315, pp. 336-341.
Thomas et al., "Adherence to various host cell lines of *Mycoplasma bovis* strains differing in pathogenic and cultural features". 2003, Veterinary Microbiology, vol. 91, pp. 101-113.
Boddie et al., "Germicidal Activities of Representatives of Five Different Teat Dip Classes Against Three *Bovine Mycoplasma* Species Using a Modified Excised Teat Model". 2002, Journal of Dairy Science, vol. 85, pp. 1909-1912.
Byrne et al., "*Mycoplasma bovis* arthritis as a sequel to respiratory disease in bought-in weanling cattle in the Republic of Ireland". Oct., 2001, Irish Veterinary Journal, vol. 54(10), pp. 516-519.
Thomas et al., "The p40* adhesin pseudogene of *Mycoplasma bovis*". 2004, Veterinary Microbiology, vol. 104, pp. 213-217.
Ghadersohi et al., "Development of a monoclonal blocking ELISA for the detection of antibody to *Mycoplasma bovis* in dairy cattle and comparison to detection by PCR". 2005, Veterinary Immunology and immunopathology, vol. 104, pp. 183-193.
Pfuetzner et al., "*Mycoplasma bovis* as an agent of mastitis, pneumonia, arthritis and genital disorders in cattle". 1996, Rev. sci. tech. Off. int. Epiz., vol. 15(4), pp. 1477-1494.
Lysnyansky et al., "Molecular characterization of the *Mycoplasma bovis* p68 gene, encoding a basic membrane protein with homology to P48 of *Mycoplasma agalactiae*". 2008, FEMS Microbiology Letters, vol. 279, pp. 234-242.
Madoff et al., "Isolation of *Mycoplasma bovis* from a Patient with Systemic Illness". Jun. 1979, Journal of Clinical Microbiology, vol. 9, No. 6, pp. 709-711.
Rodriguez et al., "Immunohistochemical Characterization of Lung Lesions Induced Experimentally by *Mycoplasma agalactiae* and *Mycoplasma bovis* in Goats". 2000, Journal of Comparative Pathology, vol. 123, pp. 285-293.
Boothby et al., "Immune Responses to *Mycoplasma bovis* Vaccination and Experimental Infection in the Bovine Mammary Gland". 1988, Canadian Journal of Veterinary Research, vol. 52, pp. 355-359.
Stalheim et al., "Naturally Occurring and Experimentally Induced Mycoplasmal Arthritis of Cattle". Sep. 1975, Journal of Clinical Microbiology, vol. 2, No. 3, pp. 165-168.
Gourlay et al., "Experimental pneumonia in conventionally reared and gnotobiotic calves by dual infection with *Mycoplasma bovis* and *Pasteurella haemolytica*". 1985, Research in Veterinary Science, vol. 28, pp. 377-382. vol. 38.
Gagea et al., "Diseases and pathogens associated with mortality in Ontario beef feedlots". 2006, Journal of Veterinary Diagnostic Investigation, vol. 18, pp. 18-28.
Alberti et al., "Molecular and antigenic characterization of a *Mycoplasma bovis* strain causing an outbreak of infectious keratoconjunctivitis". 2006, Journal of Veterinary Diagnostic Investigation, vol. 18, pp. 41-51.
Thomas et al., "Adherence of *Mycoplasma bovis* to bovine bronchial epithelial cells". 2003, Microbial Pathogenesis, vol. 34, pp. 141-148.
International Search Report for PCT/US2010/032149 mailed Aug. 5, 2010.
Written Opinion of the International Searching Authority for PCT/US2008/81545 mailed Apr. 15, 2009.

* cited by examiner

MYCOPLASMA BOVIS VACCINE AND METHODS OF USE THEREOF

RELATED APPLICATIONS

This application claims the priority benefit of U.S. Provisional Patent Application Ser. No. 60/983,482, filed on Oct. 29, 2007, and U.S. Provisional Patent Application Ser. No. 61/075,552, filed Jun. 25, 2008, the teachings and content of which are hereby incorporated by reference.

SEQUENCE LISTING

This application contains a sequence listing in paper format and in computer readable format, the teachings and content of which are hereby incorporated by reference.

BACKGROUND

*Mycoplasma bovis* (*M. bovis*) is considered to be one of the more pathogenic species of *Mycoplasma* and causes significant economic losses worldwide. Mycoplamsas cause severe clinical signs in cattle of all ages. *M. bovis* is the most frequent *Mycoplasma* pathogen found to cause pneumonia, mastitis, and arthritis in cattle and its etiological role has also been associated with otitis, keratoconjuctivitis, synovitis, and reproductive disorders in cows and bulls. In general, Mycoplasmas are difficult to treat since they lack a cell wall or membrane, which tends to make them resistant to several classes of commonly used broad-spectrum antibiotic treatments. Mycoplasmas differ from viruses in that Mycoplasmas are larger than most viruses and damage tissue cells by attaching to the surface of cells and destroying them, rather than by entering the cells. Animals infected with *M. bovis* have depressed immune responses and can exhibit signs of *M. bovis* infection such as fever, depression, anorexia, labored breathing, nasal and ocular discharge, coughing, sneezing, gasping, grunting, lameness and swollen joints, mastitis, middle ear infections, abortions, recumbence and death. The organism persists in unsanitary, warm, moist environments. Mycoplasmas can survive in milk, and even seem to thrive in the presence of large numbers of leukocytes, which are produced in response to the infection.

There are several references available in the art disclosing *M. bovis* vaccines. U.S. Pat. No. 6,548,069 discloses a vaccine composition that incorporates a whole cell inactivated bacterin containing at least two killed *M. bovis* strains. Other references available disclose passaging an *M. bovis* strain less than 10 times to prepare an inactivated vaccine, but do not describe attenuation of an infectious or pathogenic *M. bovis* strain through serial passaging or any such attenuated live *M. bovis* strain as the essence of avirulent live culture vaccine.

The prior art is deficient in that killed *M. bovis* is not as effective or efficient in lessening the severity of clinical symptoms associated with a *Mycoplasma bovis* infection. Even passage at a low level does not produce a *Mycoplasma* vaccine with high efficacy such that clinical symptoms are greatly reduced. The few low passage, inactivated, *M. bovis* vaccines that are available do not show a large reduction in the severity of clinical symptoms. Additionally, the '069 patent strongly teaches away from the idea of a high passage, attenuated strain of *M. bovis* being used in an immunogenic or vaccine composition by teaching:

"Because a *Mycoplasma* isolate may rapidly alter its antigens in culture, high passage strains of greater than about 50 passages may lose infectivity and elicit a poorer immune response when used in a bacterin of the present invention. Therefore, it is preferable to employ freshly isolated strains or cultured strains that are still virulent; that is, strains that have retained the ability to be infectious in the host animal. While no critical number of generations is known to exist, the present invention preferably starts with a *Mycoplasma* strain which has been passed no more than about ten, and preferably only about five or less times before mass scale production. By using strains with fewer generations in culture, it is believed that the antigens retain their natural state and thus will elicit a protective immune response against the infectious microorganism."

Accordingly, what is needed in the art is an immunogenic composition effective for eliciting an immunological response against *M. bovis*. What is further needed is an immunogenic composition effective for lessening the severity of or reducing the incidence of signs of *M. bovis* infection. What is still further needed is a vaccine effective for reducing or eliminating the incidence of signs of *M. bovis* infection. What is still further needed is an immunological composition effective for lessening the severity of or reducing the incidence of signs of *M. bovis* infection that can be safely administered to an animal in need thereof. What is still further needed is an immunological composition as described above that induces cross-protection and provokes an immune response against different *M. bovis* strains and isolates than those strains or isolates used in the composition. What is still further needed is a safe and effective immunological composition that is suitable as either a one dose or two dose or multi-dose (initial dose followed by booster(s)) immunization regimen, an immunological composition suitable and convenient for administration by several routes, and an immunological composition that is compatible with other immunogens and immunological compositions for preparation of combination vaccines. Finally, what is needed is an immunological composition as described above that provides rapid onset of protection and long-lasting protection to an animal in need thereof.

SUMMARY OF THE INVENTION

The immunogenic composition or vaccine of the present invention overcomes the problems present in the prior art by providing avirulent, and attenuated strains of *M. bovis*, preferably high passaged, capable of being combined with a pharmaceutically or veterinarily acceptable carrier, that can be used as an immunogenic composition with improved efficacy such that signs of *M. bovis* infection and/or the *M. bovis* infection itself and/or incidence or severity, were reduced in comparison with infection by wild-type *M. bovis* strains, preferably as well as in comparison to currently available vaccines. In other words, calves given a vaccine in accordance with the present invention are at a lower risk of developing signs of *M. bovis* infection, and any clinical signs that result would be less severe or prevalent than in animals not receiving any vaccine, but were infected with *M. bovis* or received a vaccine not in accordance with the present invention. Additionally, herds would experience a smaller number of infected animals in a herd when animals are administered the vaccine in accordance with the present invention as compared to non-vaccinated but infected animals, preferably as compared to animals vaccinated with conventional available vaccine. Advantageously, the vaccine of the present invention is a stable vaccine formulation with high efficacy that provides both quick onset and long-lasting protection. Due to the teachings of the prior art, the composition of the present invention provided surprising results in that strains of *M.*

*bovis*, preferably high passaged strains of *M. bovis* were attenuated, live, and more highly effective as components of an immunogenic composition.

The invention disclosed herein provides for, avirulent, and attenuated strains or isolates of *M. bovis*, preferably high passaged attenuated strains of *M. bovis* that elicit or provoke an immune response when administered to an animal. Advantageously, the immune response protects the animals receiving the administration of the composition of the present invention such that individual animals are a lower risk of developing signs of *M. bovis* infection, and such signs would be less severe or prevalent than in animals not receiving the composition or in animals receiving a vaccine or composition not made in accordance with the present invention.

Applicants note that for purposes of the present invention, the terms "isolate" and "strain" are used interchangeably and that differences between individual strains or isolates can be detected using DNA fingerprinting (i.e. different strains or isolates will have differing fingerprints).

In one embodiment, an immunogenic composition is disclosed which comprises a high passage strain of *M. bovis* and a pharmaceutically acceptable carrier. Preferably, said *M. bovis* strain is attenuated and avirulent. The immunogenic composition of the present invention produces an immunogenic response against *M. bovis* infection in cattle. The immunogenic response to *M. bovis* infection generated or induced by administration of the immunogenic composition greatly reduces the severity of or incidence of signs of *M. bovis* infection. In another embodiment, a method of making an immunogenic composition including a high passage strain of *M. bovis*, preferably a high passaged, attenuated, avirulent *M. bovis* strain is disclosed. In another embodiment, a method of stimulating a rapid and long lasting serological humoral immune response, and consequently disease protection, using the immunogenic composition in calves is disclosed. In yet another embodiment, a method of immunizing calves against *M. bovis* infection by administering the immunogenic composition of the present invention in an effective amount is disclosed. The immunogenic or vaccine composition of the present invention, when administered to calves subsequently challenged with a wild-type strain of *M. bovis*, exhibited a decrease in signs of *M. bovis* infection including a decrease in clinical symptoms, lung pathology, lameness, and joint pathology normally associated with *M. bovis* infection. Specifically, a reduction in lung pathology and an appreciable reduction in joint clinical symptoms and associated lameness were observed in the vaccinated group. In another embodiment of the present invention, a method for reducing signs of *M. bovis* infection is disclosed, preferably by administering any of the attenuated, avirulent *M. bovis* bacteria according to the invention and/or disclosed in the present patent applications. The reduction of signs of *M. bovis* infection is achieved by administration of the immunogenic composition of the present invention.

In one preferred embodiment of the present invention, calves were administered one of three live vaccines or immunogenic compositions, each comprising a high passage, attenuated strain of *M. bovis* and a pharmaceutically acceptable carrier. The *M. bovis* high passage strains are preferably passaged more than 10, preferably at least 20, still more preferably at least 30, even more preferably at least 40, still more preferably, at least 50, even more preferably at least 55, still more preferably at least 60, even more preferably at least 70, still more preferably, at least 80, even more preferably at least 90, still more preferably at least 95, even more preferably at least 100, still more preferably at least 102 times, and most preferably at least 106 times, preferably in vitro in cell culture. The strains of *M. bovis* useful in the vaccine or immunogenic composition can be any strain or isolate. Three representative strains include 052823A106, deposited with the American Type Culture Collection (ATCC) 10801 University Boulevard, Manassas, VA 20110-2209 on Oct. 16, 2007 under the terms of the Budapest Treaty and designated as PTA-8694; 05249A102, also deposited with the ATCC in Manassas, VA on Oct. 16, 2007 under the terms of the Budapest Treaty and designated as PTA 8696; and 0519021B106, also deposited with the ATCC in Manassas, VA on Oct. 16, 2007 and designated as PTA 8695. Each of these strains prior to passaging are pathogenic, but after passaging each of these strains as described above, and particularly after passaging more than 100 times, the resultant passaged strains were attenuated, avirulent, and produced an immune response in an animal receiving an administration of the immunogenic composition of the strain. The calves were subsequently challenged with *M. bovis* isolates obtained from naturally occurring disease outbreaks. In all instances herein, the challenge isolates had a different "fingerprint" (as determined below) than the isolates used for vaccination (i.e. it was a heterologous challenge). Advantageously, the administration of the passaged strains resulted in immune responses that reduced the severity and/or incidence of clinical symptoms of *M. bovis* infection after challenge with a pathogenic strain or wild-type strain of *M. bovis*.

Thus, according to a further aspect the present invention relates to any of the attenuated *M. bovis* bacteria strains deposited with the ATCC under accession numbers PTA-8694; PTA 8695; or PTA 8696, preferably as well as to any attenuated descendant *M. bovis* bacteria strains of any of the foregoing deposited *M. bovis* bacteria strains that can be used in an immunogenic composition with improved efficacy such that signs of *M. bovis* infection and/or the *M. bovis* infection itself and/or incidence or severity, were reduced in comparison with infection by wild-type *M. bovis* strains, preferably as well as in comparison to currently available vaccines, and with high efficacy that provides both quick onset and long-lasting protection.

According to another aspect, the present invention also provides immunogenic compositions as described herein, comprising any of the attenuated *M. bovis* bacteria strains deposited with the ATCC under accession numbers PTA-8694; PTA 8695; or PTA 8696, or any attenuated descendant *M. bovis* bacterium strain of any of the foregoing deposited *M. bovis* bacteria strains. Preferably, those immunogenic compositions comprising any of the attenuated *M. bovis* bacteria strains deposited with the ATCC under accession numbers PTA-8694; PTA 8695; or PTA 8696. Any of the specific foregoing *M. bovis* bacteria strains can be used Moreover, the present invention also relates to the veterinary use of any of those specific an attenuated *M. bovis* strains as described herein, e.g. for the reduction of the severity and/or incidence of clinical symptoms of *M. bovis* infection after challenge with a pathogenic strain or wild-type strain of *M. bovis*.

According to another aspect, the present invention also relates to attenuated *M. bovis* bacteria having the same characteristics as the *M. bovis* bacteria strains deposited with the ATCC under accession numbers PTA-8694; PTA 8695; or PTA 8696. The term "having the characteristics as the *M. bovis* bacteria strains deposited with the ATCC under accession numbers PTA-8694; PTA 8695; or PTA 8696" means that such a bacteria strain is attenuated, capable to induce a humoral immune response in a calf within 14 days after administration of one dose of 2.1E9 CFU via the subcutaneous or intranasal route to a calf, and do not cause clinical signs normally caused by an infection with a pathogenic *M. bovis* wild-type strain.

As a reference method, the humoral immune response is to be determined by the Biovet® (Midwestern Bio-Ag Products and Services, Inc.) *M. bovis* ELISA-Kit using the protocol provided with the test kit. Preferably, each of those strains induces a humoral immune response within 14 days after administration of one dose of 2E9 CFU via the subcutaneous or intranasal route to a calf, that has a relative ELISA score in the BIOVET® (Midwestern Bio-Ag Products and Services, Inc.) *M. bovis* ELISA-Kit using the protocol provided with the test kit of at least 1.5 when expressed as Optical Density (O.D.) readings.

The composition of the present invention can be administered in any conventional manner. Examples of administration methods include any that afford access by cells of the immune system to the immunogenic composition: oral, transdermal/intradermal, intravenous, subcutaneous, intramuscular, intraocular, intraperitoneal, intrarectal, intravaginal, intranasal, intragastrical, intratracheal, intrapulmonarial, or any combination thereof. Preferred modes of administration are intramuscular, subcutaneous and intranasal, with subcutaneous and intranasal being especially preferred. If desired or necessary, booster immunizations may be given once or several times at various intervals. After administration of such a vaccine, an immune response is elicited in the animal and signs of *M. bovis* infection are reduced in incidence and/or severity when exposed to wild-type bacteria or isolates after challenge with a virulent form of *M. bovis*. Furthermore, the vaccine or immunogenic composition of the present invention exhibited effective cross-protection against *M. bovis* strains other than the strain passaged to attenuation and then used as an antigenic component.

In preferred forms, the dose volume of the vaccine is no more than 5 ml, more preferably no more than 3 ml, and more preferably no more than 2 ml. In a most preferred embodiment, the dose would be 2 ml, preferably administered intranasally, with 1 ml being administered in each nostril, even more preferably administered subcutaneously, and most preferably administered both intranasally and subcutaneously on one occasion as a single dose. In some preferred forms, a second or subsequent administration of the immunogenic composition would be administered after the first administration. Such a subsequent administration would preferably occur at least 10 days after the initial administration, more preferably between at least 10-32 days, more preferably between at least 12-30 days, still more preferably at least 14 days, and most preferably between at least 14-28 days. In most preferred forms, the vaccine would be administered either on Day 0 as a single dose, or, in alternative forms, on Day 0 and 14-28 days thereafter with exposure to pathogenic forms of *M. bovis* not occurring until after the completion of the immunizing regimen. In a most preferred form, no booster is necessary and the vaccine is administered only one time. The vaccine is administered to animals from 1 day of age through adulthood, preferably to calves from 1 day of age through young adult cattle 2 years of age, more preferably to calves from 1 day of age through 16 weeks of age, and most preferably to calves from 6 weeks to 12 weeks of age. Such administration reduced signs of *M. bovis* infection as described below. In fact, the studies herein show that signs of *M. bovis* infection in the group vaccinated as described above were reduced by at least 50%, more preferably at least 60%, even more preferably at least 70%, and even more preferably at least 75% in comparison to the non-vaccinated group. Lung pathology assessment, specifically the percentage of lung consolidation attributed to lesions due to *M. bovis* as customarily scored for various species was made post-necropsy and was reduced when compared to the non-vaccinated group, by at least 33%, more preferably at least 50%, even more preferably at least 70%, even more preferably at least 80%, even more preferably at least 90%, and most preferably by at least 95%.

In another preferred embodiment, the vaccine of the present invention is combined with a suitable adjuvant. "Adjuvants" as used herein, can include aluminum hydroxide and aluminum phosphate, saponins e.g., Quil A, QS-21 (Cambridge Biotech Inc., Cambridge Mass.), GPI-0100 (Galenica Pharmaceuticals, Inc., Birmingham, Ala.), water-in-oil emulsion, oil-in-water emulsion, water-in-oil-in-water emulsion. The emulsion can be based in particular on light liquid paraffin oil (European Pharmacopea type); isoprenoid oil such as squalane or squalene; oil resulting from the oligomerization of alkenes, in particular of isobutene or decene; esters of acids or of alcohols containing a linear alkyl group, more particularly plant oils, ethyl oleate, propylene glycol di-(caprylate/caprate), glyceryl tri-(caprylate/caprate) or propylene glycol dioleate; esters of branched fatty acids or alcohols, in particular isostearic acid esters. The oil is used in combination with emulsifiers to form the emulsion. The emulsifiers are preferably nonionic surfactants, in particular esters of sorbitan, of mannide (e.g. anhydromannitol oleate), of glycol, of polyglycerol, of propylene glycol and of oleic, isostearic, ricinoleic or hydroxystearic acid, which are optionally ethoxylated, and polyoxypropylene-polyoxyethylene copolymer blocks, in particular the Pluronic products, especially L121. See Hunter et al., The Theory and Practical Application of Adjuvants (Ed. Stewart-Tull, D. E. S.). John Wiley and Sons, NY, pp 51-94 (1995) and Todd et al., Vaccine 15:564-570 (1997).

For example, it is possible to use the SPT emulsion described on page 147 of "Vaccine Design, The Subunit and Adjuvant Approach" edited by M. Powell and M. Newman, Plenum Press, 1995, and the emulsion MF59 described on page 183 of this same book.

A further instance of an adjuvant is a compound chosen from the polymers of acrylic or methacrylic acid and the copolymers of maleic anhydride and alkenyl derivative. Advantageous adjuvant compounds are the polymers of acrylic or methacrylic acid which are cross-linked, especially with polyalkenyl ethers of sugars or polyalcohols. These compounds are known by the term carbomer (Phameuropa Vol. 8, No. 2, June 1996). Persons skilled in the art can also refer to U.S. Pat. No. 2,909,462 which describes such acrylic polymers cross-linked with a polyhydroxylated compound having at least 3 hydroxyl groups, preferably not more than 8, the hydrogen atoms of at least three hydroxyls being replaced by unsaturated aliphatic radicals having at least 2 carbon atoms. The preferred radicals are those containing from 2 to 4 carbon atoms, e.g. vinyls, allyls and other ethylenically unsaturated groups. The unsaturated radicals may themselves contain other substituents, such as methyl.

The products sold under the name Carbopol® ; Lubrizol Advanced Materials, Inc., Ohio, USA) are particularly appropriate. They are cross-linked with an allyl sucrose or with allyl pentaerythritol. Among then, there may be mentioned Carbopol® 974P, 934P and 971P. Most preferred is the use of Carbopol® 971P. Among the copolymers of maleic anhydride and alkenyl derivative, are the copolymers EMA (Monsanto) which are copolymers of maleic anhydride and ethylene. The dissolution of these polymers in water leads to an acid solution that will be neutralized, preferably to physiological pH, in order to give the adjuvant solution into which the immunogenic, immunological or vaccine composition itself will be incorporated.

Further suitable adjuvants include, but are not limited to, the RIBI adjuvant system (Ribi Inc.), Block co-polymer (CytRx, Atlanta Ga.), SAF-M (Chiron, Emeryville Calif.), monophosphoryl lipid A, Avridine lipid-amine adjuvant, heat-labile enterotoxin from E. coli (recombinant or otherwise), cholera toxin, IMS 1314 or muramyl dipeptide, or naturally occurring or recombinant cytokines or analogs thereof or stimulants of endogenous cytokine release, among many others.

Preferably, the adjuvant is added in an amount of about 100 μg to about 1 g per dose. Even more preferably the adjuvant is added in an amount of about 100 μg to about 500 mg per dose. Even more preferably the adjuvant is added in an amount of about 500 μg to about 250 mg per dose. Even more preferably the adjuvant is added in an amount of about 750 μg to about 100 mg per dose. Even more preferably the adjuvant is added in an amount of about 1 mg to about 50 mg per dose. Even more preferably the adjuvant is added in an amount of about 1 mg to about 10 mg per dose. Most preferably the adjuvant is added in an amount of about 1 mg per dose.

In addition, the immunogenic and vaccine compositions of the present invention can include one or more veterinary-acceptable carriers. As used herein, "a veterinary-acceptable carrier" includes any and all solvents, dispersion media, coatings, adjuvants, stabilizing agents, diluents, preservatives, antibacterial and antifungal agents, isotonic agents, adsorption delaying agents, and the like. In some preferred embodiments, and especially those that include lyophilized immunogenic compositions, stabilizing agents for use in the present invention include stabilizers for lyophilization or freeze drying.

"Diluents" can include water, saline, dextrose, ethanol, glycerol, and the like. Isotonic agents can include sodium chloride, dextrose, mannitol, sorbitol, and lactose, among others. Stabilizers include albumin and alkali salts of ethylendiamintetracetic acid, among others.

An "immunogenic or immunological composition" refers to a composition of matter that comprises at least one antigen, which elicits an immunological response in the host of a cellular and/or antibody-mediated immune response to the composition or vaccine of interest. Usually, an "immunological response" includes but is not limited to one or more of the following effects: the production or activation of antibodies, B cells, helper T cells, suppressor T cells, and/or cytotoxic T cells and/or gamma-delta T cells, directed specifically to an antigen or antigens included in the composition or vaccine of interest. Preferably, the host will display either a therapeutic or protective immunological response such that resistance to new infection will be enhanced and/or the clinical severity of the disease reduced. Such protection will be demonstrated by either a reduction or lack of clinical signs normally displayed by an infected host, a quicker recovery time and/or a lowered duration or bacterial titer in the tissues or body fluids or excretions of the infected host.

"Signs of M. bovis infection" refers to the manifestations of infection or disease caused by M. bovis including both the clinical symptom(s) and pathology typically experienced by cattle infected with wild type M. bovis. These manifestations of infection or disease may take many forms including, but not limited to, fever, depression, anorexia, labored breathing, nasal and ocular discharge, coughing, sneezing, gasping, grunting, lameness and swollen joints, middle ear infections, discharge from inflammation of the inner ear, abortions and other reproductive disorders, recumbence, respiratory infection, head tilt, ataxia, arthritis, mastitis, otitis, keratoconjunctivitis, synovitis, pleuritis, lung lesions, lung consolidation and nodular formation in the lungs, increased synovial fluid, thickened joint capsules, and even death.

"High Passage strain" for purposes of this disclosure, refers to an M. bovis strain that has been passaged more than 10, preferably at least 20, still more preferably at least 30, even more preferably at least 40, still more preferably, at least 50, even more preferably at least 55, still more preferably at least 60, even more preferably at least 70, still more preferably, at least 80, even more preferably at least 90, still more preferably at least 95, even more preferably at least 100, still more preferably at least 102 times, and most preferably at least 106 times in vitro in cell culture.

"Lung Pathology Assessment" refers to observation of the lungs after necropsy, including, but not limited to, assessment of consolidation, lesions, and nodular formations as well as assessment of the thoracic cavity including pleuritis and fluid accumulation.

"Attenuation" means reducing the virulence of a pathogen. In the present invention "attenuation" is synonymous with "avirulent". In the present invention, an attenuated bacterium is one in which the virulence has been reduced so that it does not cause clinical signs of a M. bovis infection but is capable of inducing an immune response in the target mammal, but may also mean that the clinical signs are reduced in incidence or severity in animals infected with the attenuated M. bovis in comparison with a "control group" of animals infected with non-attenuated M. bovis and not receiving the attenuated bacterium. In this context, the term "reduce/reduced" means a reduction of at least 10%, preferably 25%, even more preferably 50%, most preferably of more than 100% as compared to the control group as defined above. Thus, an attenuated, avirulent M. bovis strain is one that suitable for incorporation into an immunogenic composition, comprising a modified live M. bovis bacterium.

An "effective amount" for purposes of the present invention, means an amount of an immunogenic composition capable of inducing an immune response that reduces the incidence of or lessens the severity of M. bovis infection in an animal. Particularly, an effective amount refers to 10E3 to 10E10, preferably to 10E6 to 10E10 colony forming units (CFU) per dose.

"Improved efficacy such that clinical signs associated with M. bovis infection and/or the M. bovis infection itself were reduced in comparison to currently available vaccines when vaccinates are exposed to M. bovis or suffer infection by wild-type M. bovis strains" refers to a reduction in either the incidence of or severity of clinical signs of M. bovis infection when comparing vaccines made from strains passaged as taught by the present invention with M. bovis vaccines that were available prior to this invention. In this context, animals not vaccinated, or vaccinated with M. bovis vaccines available prior to the present invention will have clinical signs of M. bovis infection that are at least 30%, and possibly up to more preferably at least 40%, still more preferably at least 50%, even more preferably at least 60%, still more preferably at least 70%, even more preferably at least 75%, still more preferably at least 80%, even more preferably at least 85%, still more preferably at least 90%, and most preferably at least 95% more severe or prevalent than in animals receiving an administration of an M. bovis immunogenic composition in accordance with the present invention.

"Long-lasting protection" shall refer to "improved efficacy" that persists for at least 3 weeks, but more preferably at least 6 months, still more preferably at least 1 year, even more preferably at least 2 years for beef animals, and at least 6 months, more preferably at least 1 year, still more preferably at least 2 years, still more preferably at least 3 years, and even more preferably at least 4 years for dairy animals. For both dairy animals and beef animals, it is most preferred that the long lasting protection shall persist until the average age at which beef animals are marketed for meat and the age at which dairy animals conclude their productive life of milking.

The term "in need of such administration" or "in need of such administration treatment", as used herein means that the administration/treatment is associated with the boosting or improvement in health or any other positive medicinal effect on health of the animals which receive the immunogenic composition in accordance with the present invention.

"DNA fingerprinting", as used herein, refers to the rapid identification of bacterial strains accomplished by amplifying the DNA between insertion sequences and measuring the pattern of amplified products as described in WO2008-030619. Briefly, using PCR and a combination of outwardly facing primers designed against bacterial insertion sequences (transposable elements), patterns are produced that are unique to an isolate of a bacterial species. These patterns can then be compared for such things as epidemiology or phylogeny. One preferred method of DNA fingerprinting utilizes PCR and a combination of outwardly facing primers designed against single or multiple bacterial insertion sequences. Such a method produces amplification products from adjacent IS. Once the PCR amplification is complete, the products are separated (agar gel) and banding patterns are produced, according to the molecular weight of the amplification products, which are unique to an isolate of a bacterial species. The preferred method is to carry out multiplex PCR using outwardly facing primers. Multiplex PCR is a variant of PCR which enables simultaneous amplification of many targets of interest in one reaction by using multiple primer sets. Of course, other molecular-based fingerprinting methods known in the art may also be used.

An "insertion sequence" (IS) is a short DNA sequence that acts as a transposable element. IS are generally around 700 to 2500 bp in length, which is relatively small compared to other types of transposable elements. They code for proteins implicated in transposition activity, wherein the proteins catalyze the enzymatic reaction allowing the IS to move. IS elements are unique to a particular species or can be shared between taxonomic groups. There are usually multiple copies of these insertion sequences, but they are located in unique locations for a specific transposable element.

Thus, according to another aspect the present invention relates to the use of an *M. bovis* strain, attenuated through multiple passage or serial attenuation as described above, as a medicine, preferably as a veterinary medicine.

According to another aspect of the present invention, *M. bovis* strains attenuated as described above can be used for the preparation of a pharmaceutical composition, as described herein, for the prophylaxis or treatment of infections caused by *M. bovis*. As noted above, those pharmaceutical compositions/vaccine compositions can be used for the treatment and/or prophylaxis of animals susceptible to infection by *M. bovis*.

In another aspect of the present invention, the invention is a method for the treatment or prophylaxis including a lessening of the incidence of wild type infection in a herd or reduction in the severity of signs of *M. bovis* infection associated with wild type *M. bovis* infected animals administered immunogenic compositions in accordance with the present invention in comparison to animals that are either not vaccinated or vaccinated with vaccines available prior to the present invention is provided. Additionally, administration of the vaccine in accordance with the present invention reduces the number of animals in a herd that become infected with *M. bovis*. Such a method generally involves the administration of a therapeutically effective amount of an *M. bovis* strain attenuated through the methods disclosed above, to a subject or herd of subjects in need of such a treatment. Preferably, clinical symptoms are lessened in incidence or severity by at least 10%, more preferably by at least 20%, still more preferably by at least 30%, even more preferably by at least 40%, still more preferably by at least 50%, even more preferably by at least 60%, still more preferably by at least 70%, even more preferably by at least 80%, still more preferably by at least 90%, and most preferably by at least 95% in comparison to animals that are either not vaccinated or vaccinated with an *M. bovis* immunogenic composition that was available prior to the present invention but subsequently infected by wild-type *M. bovis*.

DETAILED DESCRIPTION OF THE PREFERRED EMBODIMENTS

Figure 1:
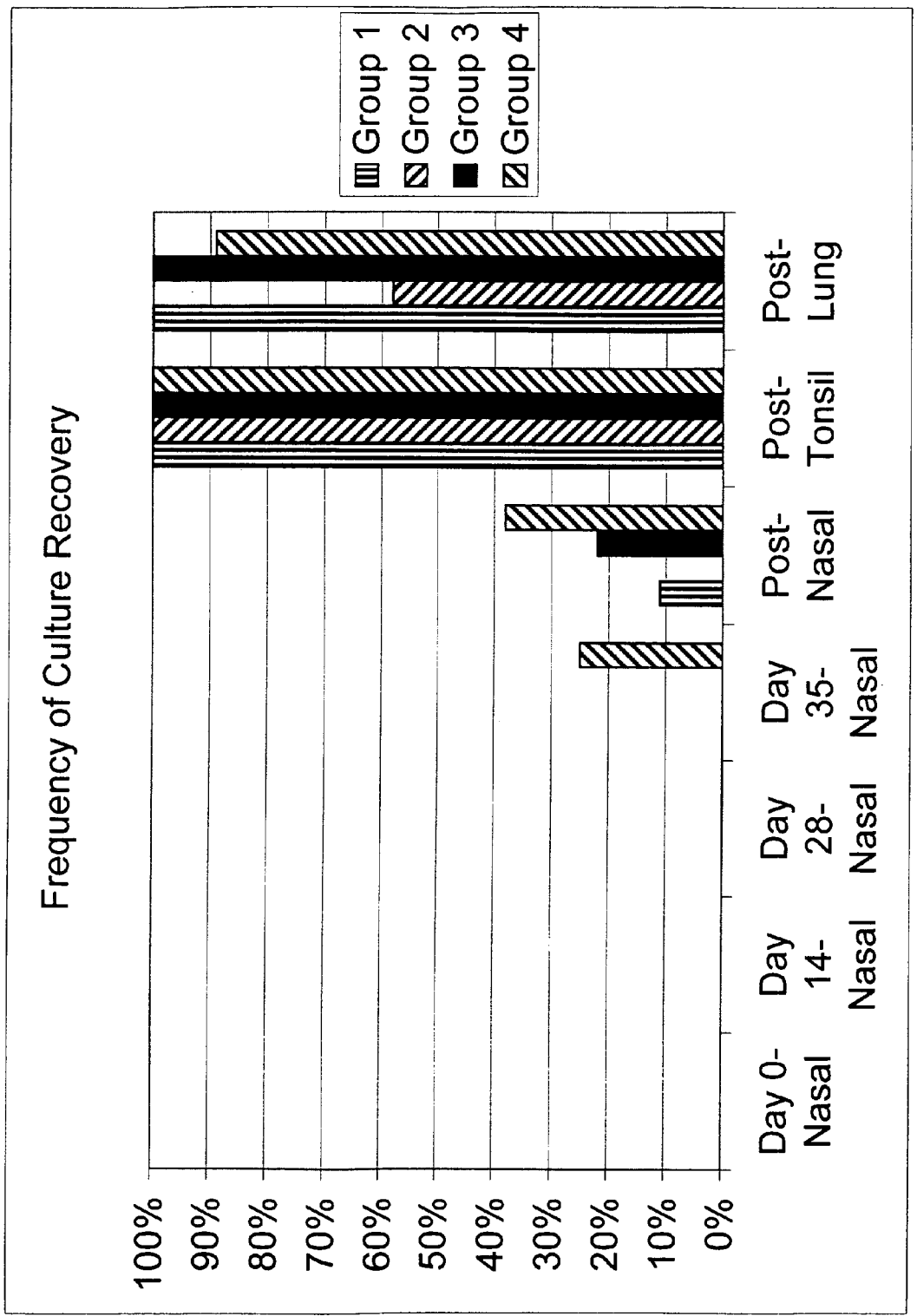
FIG. 1: Frequency of Culture Recovery from Nasal, Tonsil and Lung Samples (Days 0, 14, 28, and Post)

The following examples are representative of preferred embodiments of the present invention. It is understood that nothing herein should be taken as a limitation upon the overall scope of the invention.

EXAMPLE 1

This Example assessed the efficacy of an experimental live *M. bovis* vaccine using two different challenge models in a target species.

Materials and Methods

Thirty-five colostrum deprived (CD) Holstein calves ranging in age from 4-8 weeks of age were used. All animals met the inclusion criteria, namely that they tested negative for *M. bovis* and were in good health at the time of the challenge. The calves were first randomly assigned to 1 of 4 groups. Groups 1-3 each contained 9 calves, and Group 4 contained 8 calves. Group 1 and 2 calves were vaccinated with Live Vac 1, which is a raw culture of *M. bovis* isolate 052823 passaged 106 times 05283A106(ATCC Designation No. PTA-8694) while Group 3 and 4 calves were vaccinated with media only. The vaccine isolate for Groups 1 and 2 was obtained from naturally occurring disease outbreak and then serially passaged 106 times in *M. bovis* appropriate media. The culture was grown 24 ±2 hours at 37° C. after inoculation with an appropriate volume of seed culture determined before the study. The isolate was used without dilution. The average pre and post vaccination concentration was found to be 2.1E9 CFU/ml. The vaccine was administered in 2 ml doses subcutaneously and in 2 ml doses intranasally (1 ml in each nostril). All study calves were challenged with virulent *M. bovis* to induce the naturally occurring infection and disease with Groups 1 and 3 receiving a higher challenge dose and Groups 3 and 4 receiving a lower challenge dose The doses and administrations of the test substance are summarized in Table 1.

TABLE 1

| Group Treatments | | | | | | | |
|---|---|---|---|---|---|---|---|
| | | Test Substance | | | Challenge | | |
| Groups | Animals/ group | Article | Dose/ Route | Admin Schedule | Material | Dose | Admin Schedule |
| Group 1 | 9 | *M. bovis* Live I | 2 ml SQ and 2 ml IN (1 ml each nostril) | Day 0 and 14 | *M. bovis* (Single Isolate Fresh) | High dose of challenge material and 30 ml of PBS | Day 29 (approx 4 weeks after vaccination) |
| Group 2 | 9 | *M. bovis* Live I | 2 ml SQ and 2 ml IN (1 ml each nostril) | Day 0 and 14 | *M. bovis* (Single Isolate Fresh) | Low dose of challenge material and 30 ml of PBS | Day 29 (approx 4 weeks after vaccination) |
| Group 3 | 9 | Media Only | 2 ml SQ and 2 ml IN (1 ml each nostril) | Day 0 and 14 | *M. bovis* (Single Isolate Fresh) | High dose of challenge material and 30 ml of PBS | Day 29 (approx 4 weeks after vaccination) |
| Group 4 | 8 | Media Only | 2 ml SQ and 2 ml IN (1 ml each nostril) | Day 0 and 14 | *M. bovis* (Single Isolate Fresh) | Low dose of challenge material and 30 ml of PBS | Day 29 (approx 4 weeks after vaccination) |

Nasal swabs and blood samples were taken on Days 0, 14, 28, 35, and 42. At necropsy, samples of the lungs were taken, tonsil swabs were collected from all calves and joint swabs were taken from animals with clinical abnormalities. Additionally, samples were taken from other locations in certain animals showing area involvement. In all cases, three sterile swabs were rubbed around the regions, as aseptically as possible, for a few seconds and then removed. Two of the swabs were placed into individual transport containers with media and one was placed into a transport container without media. Table 2 summarizes the samples taken from each calf.

TABLE 2

| Day | Event | Samples | Testing |
|---|---|---|---|
| −42 to 0 | General Observations (Daily) | — | — |
| Approx −35 | Collect samples | Nasal swab (Wet/Dry)<br>Blood (SST)<br>Ear-notch | *M. bovis* (Culture/PCR)<br>*M. bovis* (ELISA)<br>BVDV (IHC) |
| 0 to 28 | Clinical assessment | — | — |
| 0 | Collect samples | Nasal swab (Wet/Dry)<br>Blood (SST) | *M. bovis* (Culture/PCR)<br>*M. bovis* (ELISA) |
| | $1^{st}$ Vaccination | — | — |
| 14 | Injection site evaluation. | — | — |
| | Collect samples | Nasal swab (Wet/Dry)<br>Blood (SST) | *M. bovis* (Culture/PCR)<br>*M. bovis* (ELISA) |
| | 2nd Vaccination | — | — |
| 28 | Collect samples | Nasal swab (Wet/Dry)<br>Blood (SST) | *M. bovis* (Culture/PCR)<br>*M. bovis* (ELISA) |
| | Injection site evaluation | — | — |
| 29 | Challenge | — | — |
| 28 to 43 | Clinical observation (Daily) | — | — |
| 35 | Collect samples | Nasal swab (Wet/Dry)<br>Blood (SST) | *M. bovis* (Culture/PCR)<br>*M. bovis* (ELISA) |
| 42 | Collect samples | Nasal swab (Wet/Dry)<br>Blood (SST) | *M. bovis* (Culture/PCR)<br>*M. bovis* (ELISA) |
| 43 | Necropsy and Gross Pathology | — | — |
| | Collect samples (Post) | Tonsil swab (Wet/Dry)<br>Lung Tissue (Preserved) | *M. bovis* (Culture/PCR)<br>*M. bovis* (IHC) |

TABLE 2-continued

| Day | Event | Samples | Testing |
|---|---|---|---|
| | | Lung Tissue (Fresh) | M. bovis (Culture/PCR) |
| | | Joint swabs (Wet/Dry) | M. bovis (Culture/PCR) |

Testing

For microbiological testing, swabs were placed in the transport media and tissue samples were shipped for M. bovis isolation. Briefly, swabs were swirled in 5 ml Mycoplasma selective broth. A small sample (approximately 5 mm) was cut from lung tissue and homogenized in 2 ml of *Mycoplasma* media. 100 μl of homogenate was added to the *Mycoplasma* selective broth. Cultures were incubated at 37 C/5% CO2. After 4-14 days, the broth was examined for growth and subcultured to plates for isolation. All positive subculture samples were stored at −70 C.

For PCR, swabs from each calf not placed in transport media and tissue samples were shipped for DNA extraction and testing by PCR using primers and probes specific for the uvrC gene of *M. bovis*. Results of PCR testing were expressed as positive or negative for *M. bovis* DNA detection.

For serology testing, serum samples were tested using a commercially available ELISA (Biovet, Canada) using the protocol provided with the test kit. ELISA results were expressed as Optical Density (OD) readings. Sample OD's were compared to the Positivity level (Mean ODp×0.3) established by the positive control included in the test kit. Positive results were then interpreted by the following scale:

| Interval | Interpretation |
|---|---|
| OD sample < Positivity Level | Negative (0) |
| Positivity Level < OD Sample <1.75 * Positivity Level | +1 |
| 1.75 * Positivity Level < OD Sample <2.3 * Positivity Level | +2 |
| 2.3 * Positivity Level < OD Sample <3 * Positivity Level | +3 |
| OD Sample <3 * Positivity Level | +4 |

For histopathology/IHC testing, formalin-fixed tissues were tested by hematoxylin/eosin stained slide and immunohistochemistry using monoclonal antibodies specific for *M. bovis*.

For clinical testing, daily general observations were carried out from Day 0 to Day 28, and then daily clinical observations were made from Day 28 to euthanasia and necropsy. Clinical and general observations that deviated from the norm were noted and documented.

At necropsy, the thoracic cavity and trachea were examined for each calf and gross observations recorded. The lungs and about 6 inches of trachea from each calf were removed intact for further examination and sample collection. For each set of lungs, the dorsal and ventral lung surfaces were photographed with an appropriate ear tag alongside each view.

For lung pathology, each lung lobe was examined by visualization and by palpation in order to determine how much pathology was present (as a percent) per each lung lobe due to *M. bovis*. Each lung lobe percent was then weighted and summed to determine the percentage of total lung with pathology.

Joint pathology was tested by examining affected joints and recording gross observations.

For data analysis purposes, data was summarized. Percent reduction of clinical symptoms and gross pathology were calculated using the following formula: % Reduction=[1−(Treatment/Non-treatment)]*100.

Additionally, 1 animal from each of groups 2 and 3, and 2 animals from group 4 were removed for humane reasons at Day 37.

Results

Pre-challenge clinical assessments were made from Day 1-Day 26. Loose/watery stool, depression, ear droop, and lethargy were observed during this phase of the study. Appropriate veterinary care was administered. No adverse site reactions or *Mycoplasma* specific clinical symptoms were noted from any groups on any day of observation. Post-challenge clinical assessments were made from Day 27-43. Coughing, labored respiration, depression, anorexia, swollen joints, lameness, and droopy ear were all clinical observations noted during this phase of the study. The incidence of clinical scores during the post-challenge period is summarized below in Table 3. Group 1 had two out of nine calves affected with at least one clinical sign of infection, two that were affected with respiratory signs and one that was affected with signs of joint infection. Group 3 had all calves affected with at least one clinical sign, seven calves affected with respiratory signs and three calves affected with signs of infection in their joints. Group 2 had four out of nine calves affected by at least one clinical sign, no calves affected with just respiratory signs, and four calves with signs of infection in their joints. Group 4 had seven calves with at least one clinical sign, one with respiratory signs, and seven with signs of infection in their joints.

TABLE 3

| | All (Respiratory + Joint + Other) | | | Respiratory | | | Joint | | |
|---|---|---|---|---|---|---|---|---|---|
| Group | Affected | Frequency | % Reduction | Affected | Frequency | % Reduction | Affected | Frequency | % Reduction |
| 1 Vac/Hi | 2/9 | 22% | 78% | 2/9 | 22% | 72% | 1/9 | 11% | 67% |
| 3 No Vac/Hi | 9/9 | 100% | | 7/9 | 78% | | 3/9 | 33% | |
| 2 Vac/Lo | 4/9 | 44% | 50% | 0/9 | 0% | 100% | 4/9 | 44% | 50% |
| 4 No Vac/Lo | 7/8 | 88% | | 1/8 | 13% | | 7/8 | 88% | |

Group 1 = Vaccine/High Respiratory Challenge
Group 2 = Vaccine/Low Respiratory Challenge
Group 3 = No Vaccine/High Respiratory Challenge
Group 4 = No Vaccine/Low Respiratory Challenge Lungs were collected at necropsy and observed for lesions associated with *M. bovis* infection. Animals exhibited variability in pathological features such as consolidation and nodular formation. Results of lung involvement were expressed as a percent using a scoring system reflecting the percentage of the total lung with gross pathology associated with *M. bovis* infection. In some cases, the determination of lung percent was hampered by adhesions or the atypical nature of lesions. Table 4 displays the ratios of individuals displaying any amount of lung lesions and percent range/average percent lung involvement. For lung pathology scores, At necropsy, joints from animals that previously exhibited clinical symptoms (swelling or lameness) were examined for gross pathology. Areas affected varied by animal and may have involved the carpus, hock, stifle, fetlock and/or elbow. Animals presented with gross swelling, increased synovial fluid, abnormal fluid appearance and thickening of the joint capsule. In more severely affected calves, fibrin was present as was erosion of the articular surface. Samples of joint fluid and/or surface swabs were tested by culture for the presence of *M. bovis*. The presence of gross pathological features in the joint is summarized in Table 5 below.

TABLE 5

Presence of Gross Pathologic Features in the Joint (0 = Normal; 1 = Abnormal)

| Group | Animals | Joint | Gross Swelling | Synovial Fluid Volume | Synovial Fluid appearance | Fibrin Present | Joint Capsule | Articular Surface | Detection of *M. bovis* |
|---|---|---|---|---|---|---|---|---|---|
| 1 | 5982 | Right Stifle | 1 | 1 | 1 | 1 | 1 | 1 | Yes |
| 1 | 5887 | Left Stifle | NR | 1 | 0 | 0 | 0 | 0 | No |
| 1 | 5007 | Right Stifle | NR | 1 | 0 | 0 | 0 | 0 | No |
| 1 | 0007 | Right rear fetlock | 0 | 0 | 0 | 0 | 0 | 0 | No |
| 2 | 5987 | Right Elbow | 0 | 0 | 0 | 0 | 0 | 0 | Yes |
| 2 | 5989 | Right Hock | NR | 1 | NR | 1 | 1 | 0 | Yes |
| 3 | 5995 | Right Hock | 1 | 1 | 1 | 1 | 1 | 0 | Yes |
| 3 | 5990 | Left Stifle | 0 | 1 | 1 | 0 | 0 | 0 | Yes |
| 4 | 5985 | Left rear fetlock | 1 | 1 | 1 | 0 | 1 | 0 | Yes |
| 4 | 5991 | Left rear fetlock | 1 | 0 | 1 | 0 | 1 | 0 | No |
| 4 | 0004 | Left Stifle | 1 | 1 | NR | 1 | 1 | 0 | Yes |
| 4 | 0000 | Left Carpus | 1 | 1 | 0 | 0 | 0 | 0 | Yes |
| 4 | 0011 | Right Elbow | 1 | 1 | 1 | 0 | 0 | 0 | Yes |
| 4 | 0011 | Right Stifle | 1 | 1 | 1 | 0 | 1 | 0 | Yes |
| 4 | 0013 | Left Stifle | 0 | 0 | 1 | 0 | 0 | 0 | No |
| 4 | 6015 | Right Hock | 0 | 1 | 1 | 1 | 0 | 0 | Yes |

Group 1 = Vaccine/High Respiratory Challenge; 2 = Vaccine/Low Respiratory Challenge; 3 = No Vaccine/High Respiratory Challenge; 4 = No Vaccine/Low Challenge
(NR = Not Recorded)

group 3 had the most calves affected (9/9) and group 2 had the least number of calves affected (2/9).

TABLE 4

Summary of Lung Pathology Scores

| | | Lung Pathology | | |
|---|---|---|---|---|
| Group | Affected | % Range | % AVG ± STD | % Reduction |
| 1 Vac/Hi | 6/9 | 0.8-26.7 | 4.0 ± 8.6 | 33% |
| 3 No Vac/Hi | 9/9 | 0.4-23.9 | 6.0 ± 7.4 | |
| 2 Vac/Lo | 2/9 | 0.4-2.0 | 0.3 ± 0.7 | 96% |
| 4 No Vac/Lo | 6/8 | 0.4-36.3 | 7.2 ± 12.3 | |

Figure 2:
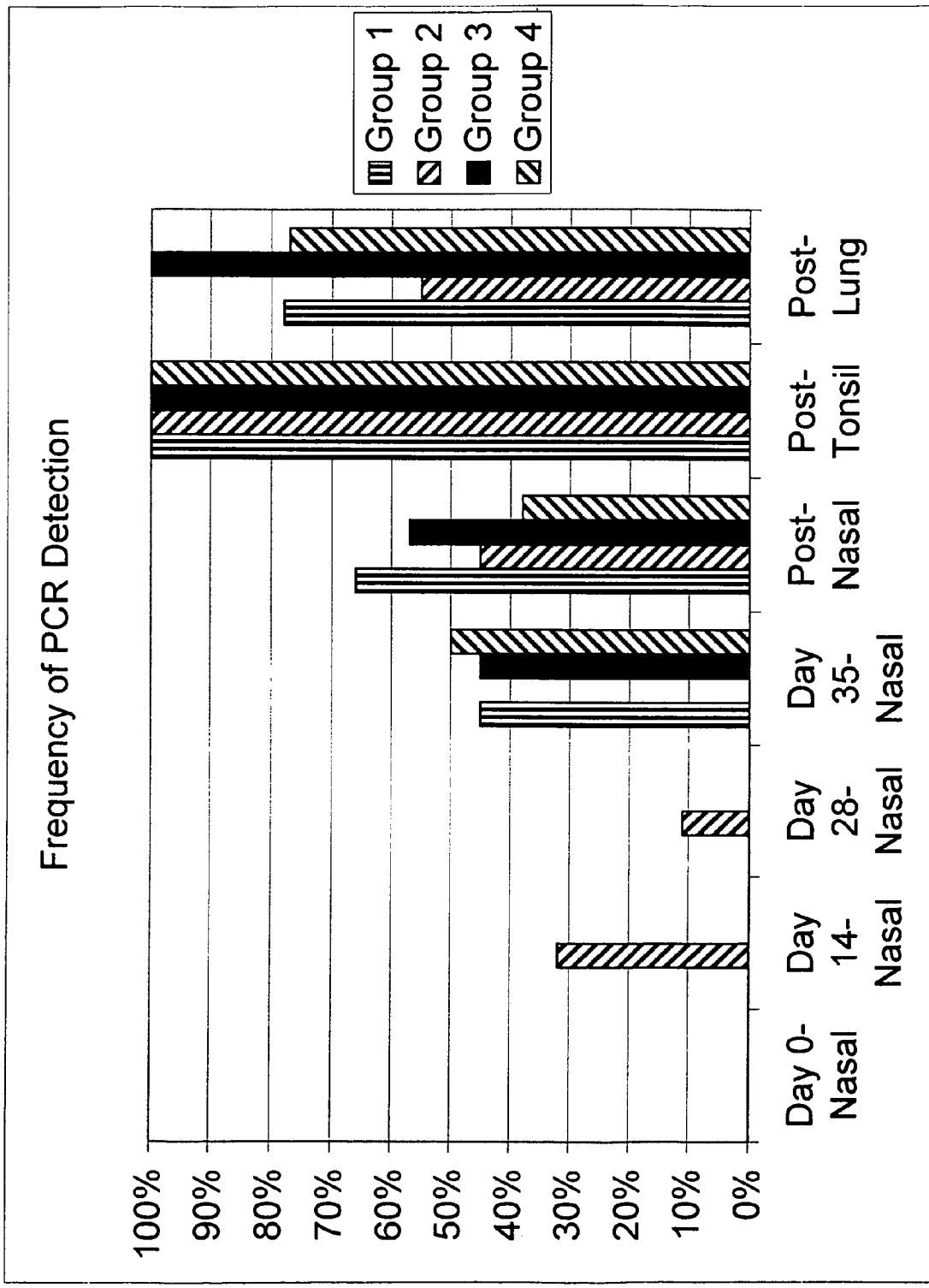
FIG. 2: Frequency of PCR Detection from Nasal, Tonsil and Lung Samples (Days 0, 14, 28, and Post)
Figure 3:
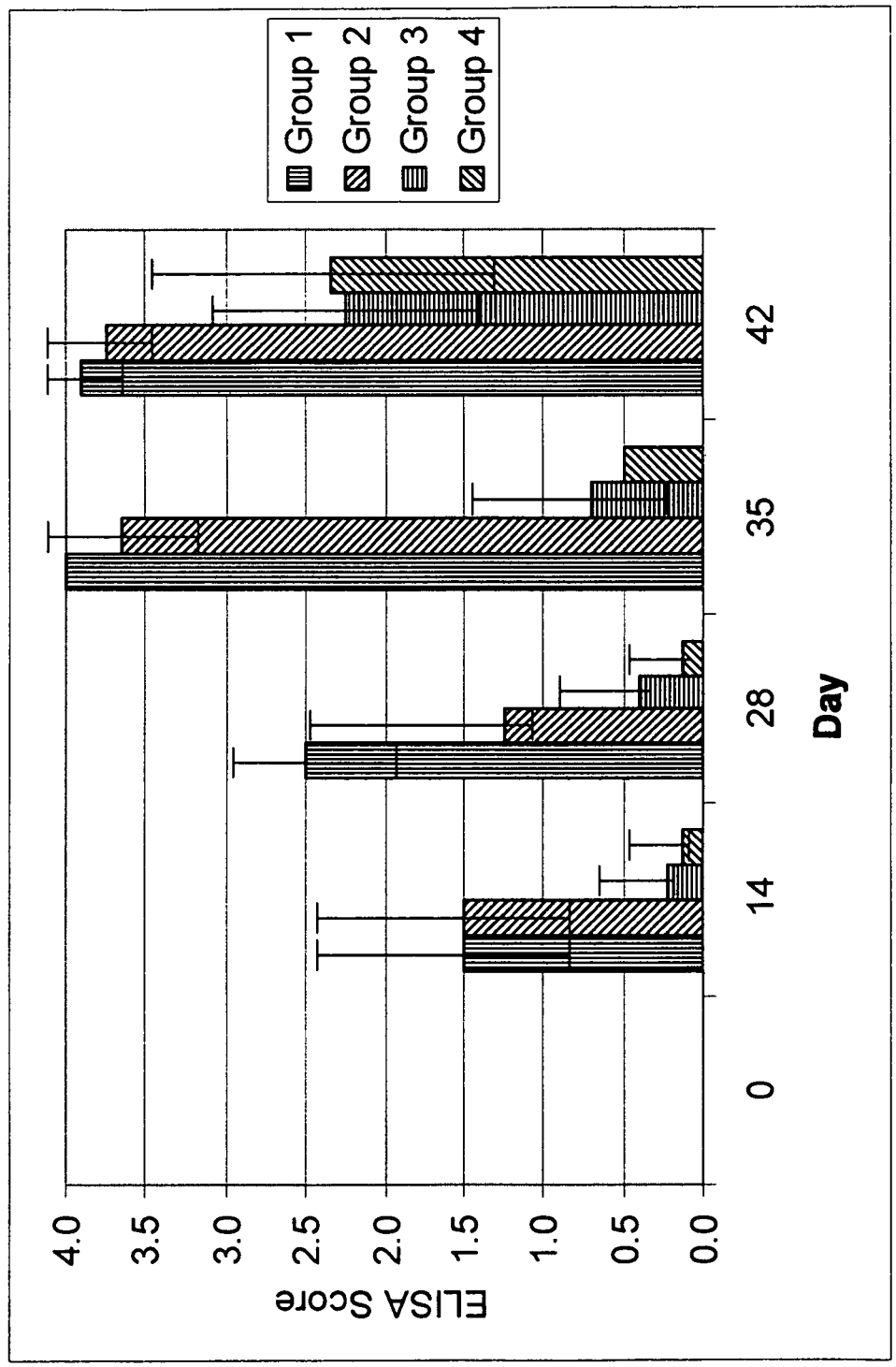
FIG. 3: Average Group Score for *M. bovis* specific Antibodies from Serum Samples (Days 0, 14, 28, 35 and 42)

The nasal passages were sampled by swab on Day 0, 14, 28, and 35 and then sampled at necropsy (Day 43). In addition, during the post-mortem, samples of tonsils were taken by swab and representative lung tissue was recovered. FIGS. 1 and 2 show the frequency of recovery by *Mycoplasma* selective culture or the frequency of detection by *M. bovis* specific PCR. As shown in FIG. 1, there was 100% recovery from all groups when the tonsils were sampled post necropsy. There was 100% recovery in groups 1 and 3 in the lungs post necropsy. Group 2 recovered the least amount from the lungs (about 60%) and group 4 recovered about 90%. No group showed recovery of bacteria *M. bovis* until samples taken nasally on day 35 of the study, and the only group to show recovery on day 35 was group 4 (25%). All groups except group 2 showed recovery in nasal samples post necropsy.

TABLE 6

Summary of PCR and Serology

| | | Day 0 | | | Day 14 | | | Day 28 | | | Day 35 | | |
|---|---|---|---|---|---|---|---|---|---|---|---|---|---|
| | | Sample | | | | | | | | | | | |
| Group | Cosby ID | Nasal Culture | Nasal PCR-uvrC | Serum ELISA | Nasal Culture | Nasal PCR-uvrC | Serum ELISA | Nasal Culture | Nasal PCR-uvrC | Serum ELISA | Nasal Culture | Nasal PCR-uvrC | Serum ELISA |
| 1 | 5981 | 0 | 0 | 0 | 0 | 0 | 2 | 0 | 0 | 3 | 0 | 1 | 4 |
| 1 | 5986 | 0 | 0 | 0 | 0 | 0 | 2 | 0 | 0 | 3 | 0 | 0 | 4 |
| 1 | 5998 | 0 | 0 | 0 | 0 | 0 | 1 | 0 | 0 | 2 | 0 | 1 | 4 |
| 1 | 5999 | 0 | 0 | 0 | 0 | 0 | 3 | 0 | 0 | 3 | 0 | 0 | 4 |
| 1 | 6003 | 0 | 0 | 0 | 0 | 0 | 1 | 0 | 0 | 2 | 0 | 0 | 4 |
| 1 | 6007 | 0 | 0 | 0 | 0 | 0 | 1 | 0 | 0 | 2 | 0 | 0 | 4 |
| 1 | 6008 | 0 | 0 | 0 | 0 | 0 | 1 | 0 | 0 | 2 | 0 | 0 | 4 |
| 1 | 6009 | 0 | 0 | 0 | 0 | 0 | 2 | 0 | 0 | 3 | 0 | 1 | 4 |
| 1 | 6012 | 0 | 0 | 0 | 0 | 0 | 1 | 0 | 0 | 2 | 0 | 1 | 4 |
| 2 | 5982 | 0 | 0 | 0 | 0 | 0 | 1 | 0 | 0 | 1 | 0 | 0 | 3 |
| 2 | 5983 | 0 | 0 | 0 | 0 | 0 | 2 | 0 | 0 | 2 | 0 | 0 | 4 |
| 2 | 5984 | 0 | 0 | 0 | 0 | 0 | 1 | 0 | 0 | 2 | 0 | 0 | 4 |
| 2 | 5987 | 0 | 0 | 0 | 0 | 0 | 1 | 0 | 0 | 1 | 0 | 0 | 3 |
| 2 | 5988 | 0 | 0 | 0 | 0 | 1 | 1 | 0 | 1 | 1 | 0 | 0 | 3 |
| 2 | 5989 | 0 | 0 | 0 | 0 | 1 | 1 | 0 | 0 | 2 | 0 | 0 | 4 |
| 2 | 5990 | 0 | 0 | 0 | 0 | 1 | 2 | 0 | 0 | 2 | 0 | 0 | 4 |
| 2 | 5992 | 0 | 0 | 0 | 0 | 0 | 2 | 0 | 0 | 3 | 0 | 0 | 4 |
| 2 | 5994 | 0 | 0 | 0 | 0 | 0 | 3 | 0 | 0 | 2 | 0 | 0 | 4 |
| 3 | 5993 | 0 | 0 | 0 | 0 | 0 | 0 | 0 | 0 | 0 | 0 | 0 | 1 |
| 3 | 5995 | 0 | 0 | 0 | 0 | 0 | 0 | 0 | 0 | 1 | 0 | 1 | 1 |
| 3 | 5996 | 0 | 0 | 0 | 0 | 0 | 1 | 0 | 0 | 1 | 0 | 1 | 2 |
| 3 | 5997 | 0 | 0 | 0 | 0 | 0 | 0 | 0 | 0 | 0 | 0 | 0 | 0 |
| 3 | 6000 | 0 | 0 | 0 | 0 | 0 | 0 | 0 | 0 | 0 | 0 | 0 | 1 |
| 3 | 6001 | 0 | 0 | 0 | 0 | 0 | 1 | 0 | 0 | 1 | 0 | 0 | 1 |
| 3 | 6002 | 0 | 0 | 0 | 0 | 0 | 0 | 0 | 0 | 0 | 0 | 1 | 0 |
| 3 | 6010 | 0 | 0 | 0 | 0 | 0 | 0 | 0 | 0 | 0 | 0 | 0 | 1 |
| 3 | 6014 | 0 | 0 | 0 | 0 | 0 | 0 | 0 | 0 | 0 | 0 | 1 | 0 |
| 4 | 5985 | 0 | 0 | 0 | 0 | 0 | 0 | 0 | 0 | 0 | 0 | 1 | 0 |
| 4 | 5991 | 0 | 0 | 0 | 0 | 0 | 0 | 0 | 0 | 0 | 1 | 1 | 0 |
| 4 | 6004 | 0 | 0 | 0 | 0 | 0 | 0 | 0 | 0 | 0 | 0 | 0 | 0 |
| 4 | 6005 | 0 | 0 | 0 | 0 | 0 | 0 | 0 | 0 | 0 | 0 | 0 | 1 |
| 4 | 6006 | 0 | 0 | 0 | 0 | 0 | 1 | 0 | 0 | 1 | 1 | 1 | 1 |
| 4 | 6011 | 0 | 0 | 0 | 0 | 0 | 0 | 0 | 0 | 0 | 0 | 0 | 0 |
| 4 | 6013 | 0 | 0 | 0 | 0 | 0 | 0 | 0 | 0 | 0 | 0 | 0 | 1 |
| 4 | 6015 | 0 | 0 | 0 | 0 | 0 | 0 | 0 | 0 | 0 | 0 | 1 | 1 |

| | | Day 42 (or Post) Sample | | | | | | | | | | |
|---|---|---|---|---|---|---|---|---|---|---|---|---|
| Group | Cosby ID | Nasal Culture | Nasal PCR-uvrC | Serum ELISA | Tonsil Culture | Tonsil PCR-uvrC | Tonsil PCR-Vac specific | Lung Culture | Lung PCR-uvrC | Lung PCR-Vac specific | Joint Culture | Joint PCR-uvrC |
| 1 | 5981 | 1 | 0 | 4 | 1 | 1 | 1 | 1 | 1 | 0 | | |
| 1 | 5986 | 0 | 1 | 4 | 1 | 1 | 1 | 1 | 1 | 0 | | |
| 1 | 5998 | 0 | 1 | 3 | 1 | 1 | 1 | 1 | 1 | 0 | | |
| 1 | 5999 | 0 | 1 | 4 | 1 | 1 | 0 | 1 | 0 | 0 | | |
| 1 | 6003 | 0 | 1 | 4 | 1 | 1 | 0 | 1 | 1 | 0 | | |
| 1 | 6007 | 0 | 0 | 4 | 1 | 1 | 1 | 1 | 1 | 0 | 0 | 0 |
| 1 | 6008 | 0 | 1 | 4 | 1 | 1 | 0 | 1 | 0 | 0 | | |
| 1 | 6009 | 0 | 1 | 4 | 1 | 1 | 0 | 1 | 1 | 0 | | |
| 1 | 6012 | 0 | 0 | 4 | 1 | 1 | 0 | 1 | 1 | 0 | | |
| 2 | 5982 | 0 | 0 | 4 | 1 | 1 | 1 | 1 | 1 | 0 | 1 | 1 |
| 2 | 5983 | 0 | 0 | 4 | 1 | 1 | 1 | 1 | 1 | 0 | | |
| 2 | 5984 | 0 | 0 | 4 | 1 | 1 | 1 | 0 | 0 | 0 | | |
| 2 | 5987 | 0 | 0 | 4 | 1 | 1 | 1 | 1 | 1 | 0 | 1 | 1 |
| 2 | 5988 | 0 | 1 | 3 | 1 | 1 | 0 | 1 | 1 | 0 | | |
| 2 | 5989 | 0 | 0 | 4 | 1 | 1 | 1 | 0 | 0 | 0 | 1 | 1 |
| 2 | 5990 | 0 | 1 | 3 | 1 | 1 | 1 | 0 | 0 | 0 | | |
| 2 | 5992 | 0 | 1 | 4 | 1 | 1 | 1 | 0 | 0 | 0 | | |
| 2 | 5994 | 0 | 1 | 4 | 1 | 1 | 1 | 1 | 1 | 0 | | |
| 3 | 5993 | 0 | 0 | 1 | 1 | 1 | 0 | 1 | 1 | 0 | | |
| 3 | 5995 | 0 | 1 | 2 | 1 | 1 | 0 | 1 | 1 | 0 | 1 | NT |
| 3 | 5996 | 0 | 1 | 3 | 1 | 1 | 0 | 1 | 1 | 0 | 1 | 1 |
| 3 | 5997 | 1 | 1 | 1 | 1 | 1 | 0 | 1 | 1 | 0 | | |
| 3 | 6000 | 1 | 1 | 3 | 1 | 1 | 0 | 1 | 1 | 0 | | |
| 3 | 6001 | 0 | 0 | 3 | 1 | 1 | 0 | 1 | 1 | 0 | | |
| 3 | 6002 | 0 | 0 | 2 | 1 | 1 | 0 | 1 | 1 | 0 | | |

TABLE 6-continued

Summary of PCR and Serology

| | | | | | | | | | | | | |
|---|---|---|---|---|---|---|---|---|---|---|---|---|
| 3 | 6010 | 0 | 1 | 3 | 1 | 1 | 0 | 1 | 1 | 0 | | |
| 3 | 6014 | 0 | 0 | 2 | 1 | 1 | 0 | 1 | 1 | 0 | | |
| 4 | 5985 | 1 | 1 | 4 | 1 | 1 | 0 | 1 | 1 | 0 | 1 | NT |
| 4 | 5991 | 1 | 1 | 2 | 1 | 1 | 0 | 1 | 1 | 0 | 0 | NT |
| 4 | 6004 | 0 | 0 | 2 | 1 | 1 | 0 | 1 | 1 | 0 | 1 | NT |
| 4 | 6005 | 0 | 0 | 3 | 1 | 1 | 0 | 1 | 0 | 0 | | |
| 4 | 6006 | 0 | 1 | 1 | 1 | 1 | 0 | 1 | 1 | 0 | 1 | 1 |
| 4 | 6011 | 0 | 0 | 1 | 1 | 1 | 0 | 0 | 0 | 0 | 1 | NT |
| 4 | 6013 | 1 | 0 | 3 | 1 | 1 | 0 | 1 | 1 | 0 | 0 | 0 |
| 4 | 6015 | 0 | 0 | 3 | 1 | 1 | 0 | 1 | 1 | 0 | 1 | 1 |

Culture
0 = No M. bovis growth
1 = Growth of *M. bovis*
M = Mixed/or other
PCR
0 = Negative for *M. bovis*
1 = Positive for *M. bovis*
ELISA
0 = Negative
1 = Positivity to 1.75x
2 = 1.75x to 2.3x
3 = 2.3x to 3.0x
4 = 3.0x or greater
NS = No Sample
NT = Not Tested All samples were tested in the Biovet *M. bovis* ELISA to monitor the serological response to *M. bovis*. Seroconversion was scored according to grouped multipliers of positivity ODs. The following table shows the average serological scores detected from each group on Day 0, 14, 28, 35 and 42. FIG. 3 shows the average group score for *M. bovis* specific antibodies from serum samples. Seroconversion indicating effective humoral immune response was detected at no more than 14 days following one dose of vaccine, and good duration of this immune response was evident by measurable serological response to *M. bovis* for at least 42 days after one vaccination and 28 days after two doses of vaccine. The score for group 1 was consistently higher than all other groups beginning on day 28. Groups 1 and 2 were equal on day 14 (1.5 ELISA score). Group 4 was the lowest from days 14-35, and came in third (about 2.2) on day 42.

Conclusions

This study assessed the efficacy of a live *M. bovis* vaccine in calves given as two doses, given both subcutaneously and intranasally, and challenge models in the target species. The challenge model included a high respiratory administration and a low respiratory administration. The study also evaluated efficacy, onset of immunity, and duration of immunity by an indirect assessment, seroconversion or humoral immune response following a single and two doses of vaccine. The onset of immunity and duration of immunity following vaccination was so proven.

Both the challenge and vaccine *M. bovis* isolates originated from different, naturally infected animals. The isolate used as the challenge was previously shown to cause both lung and joint disease during experimental challenge and predominated in mixed isolate challenge studies. The vaccine isolate is a high passage isolate (passage 106) originally derived from a diagnostic sample. Furthermore, the genotypes of the challenge and vaccine isolates were shown to be dissimilar when using the fingerprinting method described herein.

Within the high volume respiratory challenged groups (1 and 3), a reduction in respiratory clinical symptoms (72%) and lung pathology (33%) was observed in the vaccinated group. Most of the respiratory clinical symptoms in the non-vaccinated group occurred between day 2 and 3 post challenge. As shown in Table 3, the vaccine also reduced the occurrence of joint disease due to *M. bovis*.

Within the low volume respiratory challenged groups (2 and 4), a reduction (96%) in lung pathology was observed in the vaccinated group. In addition, the vaccinated group showed an appreciable reduction (50%) of joint clinical symptoms.

Laboratory testing of lung samples (IHC, PCR and culture) and joint samples (PCR and culture) agreed with gross pathology in most instances. Discrepancies may be attributed to bacterial distribution at the sampling site or between samples submitted for testing. The vaccine isolate was not detected from any lung samples tested by an experimental PCR assay designed to detect the vaccine candidate and not the challenge isolate.

The novel, high passage attenuated Live *M. bovis* vaccine candidate (052823A106) given via both intranasal and subcutaneous route administered 2 times with a 2 week interval between vaccinations was shown to be safe and effective by providing a reduction in signs of *M. bovis* infection including both clinical symptoms and pathology (respiratory and joint) associated with *Mycoplasma bovis* infection in colostrum deprived calves using various challenge conditions. The *M. bovis* vaccine and immunological composition was also effective in stimulating an onset of immunity no more than 14 days following a single dose and with a duration of at least 42 days following the single dose.

EXAMPLE 2

The purpose of this investigation was to determine the safety and efficacy of three live vaccine candidates.

Materials and Methods

The calves used for the study were 6±2 weeks of age and were divided into 6 groups. As shown in Table 7, group 1 was comprised of 10 animals, which were vaccinated with *M. bovis* Live Vaccine I on day 0 (D0) and D14 of the study. Group 1 was vaccinated with 2 ml subcutaneously and 2 ml intranasally on D0 and D14. Group 2 was comprised of 10 animals and was vaccinated with 2 ml of *M. bovis* Live Vaccine I subcutaneously on D0 and D14 of the study. Group 3 was comprised of 9 calves vaccinated with *M. bovis* Live Vaccine I on D0 and D14. Group 3 was vaccinated with 2 ml intranasally. Group 4 was a control and was not administered any vaccine. Group 5 was comprised of 2 calves that were vaccinated with *M. bovis* Live II vaccine. Group 5 was vaccinated with 2 ml subcutaneously and 2 ml intranasally on D0 and D14. Group 6 was comprised of two calves that were administered *M. bovis* Live Vaccine III. The calves in Group 6 were administered 2 ml subcutaneously and 2 ml intranasally on D0 and D14. All groups were subsequently challenged with 120 ml of challenge material. All animals were challenged on D28.

As noted in Table 8, nasal swabs were collected from all calves on Days 0, 14, 27, 35 and 41. At necropsy, tonsil swabs were collected from all calves. Joint swabs were taken from animals with clinical abnormalities. In addition, samples were taken from other locations in certain animals showing area involvement. Blood was collected from all calves on Days 0, 14, 27, 35 and 41. Blood was collected aseptically from a jugular vein from each calf. After necropsy, lungs were scored for lung lesions.

TABLE 7

Group Treatments

| | | Test Substance | | | Challenge | | |
|---|---|---|---|---|---|---|---|
| | Animals/ group | Article | Dose/ Route | Admin Schedule | Material | Dose | Admin Schedule |
| Group 1 | 10 | *M. bovis* Live I (052823 A106) | 2 ml SQ and 2 mL IN | Day 0 and 14 | *M. bovis* | challenge material with a 5 ml wash of PBS | Day 28 (approx 4 weeks after vaccination) |
| Group 2 | 10 | *M. bovis* Live I (052823 A106) | 2 ml SQ | Day 0 and 14 | *M. bovis* | challenge material with a 5 ml wash of PBS | Day 28 (approx 4 weeks after vaccination) |
| Group 3 | 9 | *M. bovis* Live I (052823 A106) | 2 mL IN | Day 0 and 14 | *M. bovis* | challenge material with a 5 ml wash of PBS | Day 28 (approx 4 weeks after vaccination) |
| Group 4 | 9 | Media Only | 2 ml SQ and 2 mL IN | Day 0 and 14 | *M. bovis* | challenge material with a 5 ml wash of PBS | Day 28 (approx 4 weeks after vaccination) |
| Group 5 | 2 | *M. bovis* Live II (05249 A102) | 2 ml SQ and 2 mL IN | Day 0 and 14 | *M. bovis* | challenge material with a 5 ml wash of PBS | Day 28 (approx 4 weeks after vaccination) |
| Group 6 | 2 | *M. bovis* Live III (0519021 B106) | 2 ml SQ and 2 mL IN | Day 0 and 14 | *M. bovis* | challenge material with a 5 ml wash of PBS | Day 28 (approx 4 weeks after vaccination) |

TABLE 8

Sample Schedule

| Day | Event | Samples | Testing |
|---|---|---|---|
| −42 to 0 | General Observations (Daily) | — | — |
| Approx −35 | Collect samples | Nasal swab (Wet/Dry)<br>Blood (SST)<br>Ear-notch | *M. bovis* (Culture/PCR)<br>*M. bovis* (ELISA)<br>BVDV (IHC) |
| 0 to 28 | Clinical assessment | — | — |
| 0 | Collect samples | Nasal swab (Wet/Dry)<br>Blood (SST) | *M. bovis* (Culture/PCR)<br>*M. bovis* (ELISA) |
| | $1^{st}$ Vaccination | — | — |
| 14 | Injection site evaluation. | — | — |
| | Collect samples | Nasal swab (Wet/Dry)<br>Blood (SST) | *M. bovis* (Culture/PCR)<br>*M. bovis* (ELISA) |
| | 2nd Vaccination | — | — |
| 27 | Collect samples | Nasal swab (Wet/Dry)<br>Blood (SST) | *M. bovis* (Culture/PCR)<br>*M. bovis* (ELISA) |
| 28 | Challenge | — | — |
| 29 to 42 | Clinical observation (Daily) | — | — |
| 35 | Collect samples | Nasal swab (Wet/Dry)<br>Blood (SST) | *M. bovis* (Culture/PCR)<br>*M. bovis* (ELISA) |
| 41 | Collect samples | Nasal swab (Wet/Dry)<br>Blood (SST) | *M. bovis* (Culture/PCR)<br>*M. bovis* (ELISA) |
| 42 | Necropsy and Gross Pathology | — | — |
| | Collect samples (Post) | Tonsil swab (Wet/Dry) | *M. bovis* (Culture/PCR) |

TABLE 8-continued

Sample Schedule

| Day | Event | Samples | Testing |
|---|---|---|---|
| | | Lung Tissue (Preserved) | *M. bovis* (IHC) |
| | | Lung Tissue (Fresh) | *M. bovis* (Culture/PCR) |
| | | Joint swabs (Wet/Dry) | *M. bovis* (Culture/PCR) |

Results and Discussion

Pre-Challenge Clinical Signs

Clinical assessments were made from Day −1 through Day 28. Loose/watery stool, ocular discharge, depression and lethargy were clinical observations noted during this phase of the study, and none were attributed to an effect of vaccination. Observation of injection sites recorded no adverse site reactions except for calf 6134 (group 6) that showed swelling at the 1$^{st}$ injection site on Day 14.

Post-Challenge Clinical Signs

Clinical observations were made from Day 28 through Day 42. Coughing, labored respiration, depression, swollen joints, lameness and droopy ear were clinical observations noted during this phase of the study. Clinical signs were divided into three types (respiratory, joint and other) typical of *Mycoplasma bovis* infection. Respiratory signs included coughing, rapid/labored respiration and nasal discharge. Joint signs included swollen joints and lameness. Other signs included ear droop, head tilt, depression and anorexia. Table 9 displaying individual results can be found below:

TABLE 9

| | | DPC | | | | | | | | | | | | | | |
|---|---|---|---|---|---|---|---|---|---|---|---|---|---|---|---|---|
| | | 0 | 1 | 2 | 3 | 4 | 5 | 6 | 7 | 8 | 9 | 10 | 11 | 12 | 13 | 14 |
| Group | ID | 28 | 29 | 30 | 31 | 32 | 33 | 34 | 35 | 36 | 37 | 38 | 39 | 40 | 41 | 42 |
| 1 | 6116 | | | | | | 5 | 4,5 | 4,5 | 4,5 | 4,5 | | | | | |
| 1 | 6123 | | | | | | | | 4,7 | 4 | 4,5 | 4,5,8 | | | | |
| 1 | 6124 | | | | | | | | | | 4,5 | 1,4,5 | 4,5,8 | 4,5 | 4,5 | 4,5 |
| 1 | 6139 | | | | | | | | | 4,5 | 1,4,5 | 4,5 | 4,5 | 4,5 | 1,4,5,8 | 4,5 |
| 1 | 6140 | | | | | | | | 4,5 | 4,5 | 4,5 | 4,5 | 4,5 | 4,5 | 4,5 | 4,5 |
| 1 | 6145 | | | | | | 5 | 4,5 | 4,5 | 4,5 | 4,5 | | | | | |
| 1 | 6151 | | | | | | 5 | 4,5 | 4,5 | 4,5 | 4,5 | 4,5 | 4,5,8 | | | |
| 1 | 6152 | | | | | | | 4 | 4,5 | 4,5 | 4,5 | 4,5 | 4,5 | 4,5 | 4,5 | 4,5 |
| 1 | 6153 | | | | | | | | | | | | | | | |
| 1 | 6156 | | | | | | 1 | | 4 | | | 4,5 | 4,5 | 4,5 | | |
| 2 | 6117 | | | | | | | 4 | 4,5 | 4,5,8 | 4,5 | | | | | |
| 2 | 6118 | | 2 | | | | | | | | | | | | | |
| 2 | 6119 | | | | | | | | | | 4 | | | 4,5 | 4,5 | |
| 2 | 6125 | | | | | 5 | 5,8 | 4,5,6,8 | 4,5 | 4,5 | 4,5 | 4,5,8 | | | | |
| 2 | 6127 | | | | | 5 | 5 | 4,5 | 4,5 | 4,5 | 4,5 | | | | | |
| 2 | 6128 | | | | | | 5 | 4,5 | 4,5 | 4,5 | 4,5 | | | | | |
| 2 | 6130 | | | | | | | | | | | 4,5 | 4,5 | 4,5 | 4,5 | 4,5 |
| 2 | 6133 | | | | | | | 4,5 | 4,5 | 4,5 | 4,5 | 4,5 | 4,5 | 4,5 | 4,5,8 | 4,5 |
| 2 | 6136 | | | | | | 4 | 4,5 | 4,5 | 4,5 | 4,5 | 4,5 | 4,5 | 4,5 | 4,5 | 4,5 |
| 2 | 6144 | | | | | | | 4,5 | 4,5 | 4,5 | 4,5 | 4,5 | 4,5 | 4,5 | 4,5 | 4,5 |
| 3 | 6129 | | | | | 5 | 5 | 4,5 | 4,5 | 4,5 | 4,5 | 4,5 | | | | |
| 3 | 6132 | | | | | | 5 | 4,5 | 4,5 | 4,5 | 4,5 | | | | | |
| 3 | 6135 | | | | | | 5 | 4,5 | 4,5 | 4,5 | 4,5 | | | | | |
| 3 | 6138 | | | | | | | | | | | | | | | |
| 3 | 6141 | | | | | | | | 4,5 | 4,5 | | 4,5 | 4,5 | 4,5 | 4,5 | 4,5 |
| 3 | 6142 | | | | | | | | | 4,5 | 4 | 4,5 | 4,5 | 4,5 | 4,5,8 | 4,5,8 |
| 3 | 6154 | | | | | | | | | 4,5 | 4,5 | 4,5 | 4,5 | 4,5 | 4,5 | 4,5 |
| 3 | 6158 | | | | | | | | | | | | | 4,5 | 4,5 | 4,5 |

TABLE 9-continued

| | | | | | | | | | |
|---|---|---|---|---|---|---|---|---|---|
| 3 | 6159 | | | | | 4,5 | 4,5,8 | 4,5 | |
| 4 | 6120 | | | 5 | | 4,5 | 4,5 | 4,5,8 | 4,5,8 |
| 4 | 6126 | | | 5 | 5 | 4,5 | 4,5 | 4,5,8 | 4,5,8 |
| 4 | 6131 | | | | | 8 | 4 | 4,5,8 | 4,5,8 |
| 4 | 6143 | | | 5 | 1,5 | 4,5 | 4,5 | 4,5,8 | 4,5,8 |
| 4 | 6146 | | | 2,5,8 | 2,4,5,8 | | | | |
| 4 | 6147 | | | | | 4,5 | 4,5 | 4,5,8 | 4,5,8 |
| 4 | 6150 | | | 1 | 1 | 4,5 | 4,5 | 1,4,5 | 4,5,8 |
| 4 | 6155 | | 5 | 5 | 4,5,8 | | | | |
| 4 | 6157 | 1,2 | 2 | 2 | 2,8 | 1,2,8 | | | |
| 5 | 6122 | | | | | | | | |
| 5 | 6137 | | | | | | | | |
| 6 | 6121 | | | | | | | | |
| 6 | 6134 | | | | | | | | |

Key to Clinical Sign:
1 Coughing
2 Rapid (labored) respiration
3 Nasal discharge
4 Swollen Joint
5 Lame
6 Ear Droop
7 Head Tilt
8 Depression
9 Anorexia
A Diarrhea
B Ocular Discharge
C Leg Laceration
Black Box = Animal removed from study

TABLE 10

Incidence of Clinical Scores during the Post-Challenge period

| | Respiratory | | | Joint | | | Early Removal | | |
|---|---|---|---|---|---|---|---|---|---|
| Group | Affected | Frequency | % Reduction | Affected | Frequency | % Reduction | Affected | Frequency | % Reduction |
| 1 Live Vac I (SQ + IN) | 3/9 | 33% | 0% | 6/9 | 67% | 33% | 4/9 | 44% | 56% |
| 2 Live Vac I (SQ) | 0/9 | 0% | 100% | 7/9 | 78% | 22% | 4/9 | 44% | 56% |
| 3 Live Vac I (IN) | 0/9 | 0% | 100% | 5/8 | 63% | 38% | 3/8 | 38% | 63% |
| 5 Live Vac II (SQ + IN) | 0/2 | 0% | 100% | 0/2 | 0% | 100% | 0/2 | 0% | 100% |
| 6 Live Vac III (SQ + IN) | 0/2 | 0% | 100% | 0/2 | 0% | 100% | 0/2 | 0% | 100% |
| 4 No Vac | 2/6 | 33% | | 6/6 | 100% | | 6/6 | 100% | |

The table 10 is subdivided into respiratory and confirmed (culture and/or PCR) joint clinicals typical of *Mycoplasma bovis* infection. In addition, early removal rates due to severe joint involvement are reported.

Lung Pathology

At necropsy, lungs were collected and observed for lesions associated with *M. bovis*. Animals exhibited variability in pathological features such as consolidation and nodular formation. Results of lung involvement were expressed as a percent using a scoring system that reflects the percentage of the total lung with gross pathology associated with *Mycoplasma bovis* infection. In some cases, determination of lung percent was hampered by adhesions or the atypical nature of lesions. Below is a table with the ratios of individuals displaying any amount of lung lesions and percent range/mean percent lung involvement.

TABLE 11

Summary of Lung Pathology Scores

| | Lung Pathology | | | |
|---|---|---|---|---|
| Group | Affected | % Range | Mean % Lesion + STD | % Lesion Reduction |
| 1 Live Vac I (SQ + IN) | 7/9 | 0.2-2.0 | 1.0 ± 0.9 | 86% |
| 2 Live Vac I (SQ) | 9/9 | 0.4-12.5 | 2.8 ± 3.8 | 61% |
| 3 Live Vac I (IN) | 5/8 | 0.2-39.2 | 6.3 ± 13.5 | 13% |
| 5 Live Vac II (SQ + IN) | 1/2 | N/A | 0.2 ± 0.3 | 98% |
| 6 Live Vac III (SQ + IN) | 0/2 | N/A | 0.0 | 100% |
| 4 No Vac | 6/6 | 2.0-19.5 | 7.2 ± 6.9 | |

Joint Pathology

At necropsy, joints from animals that previously exhibited clinical symptoms (swelling and/or lameness) were examined for gross pathology. Areas affected varied by animal and may involve the carpus, hock, stifle, fetlock and/or elbow. Animals presented with gross swelling, increased synovial fluid, abnormal fluid appearance or thickening of the joint capsule. In more severely affected calves, fibrin was present and erosion of the articular surface. Samples of joint fluid and/or surface swabs were tested by culture and PCR for the presence of *Mycoplasma* bovis. Vaccination using any of the attenuated live vaccines successfully reduced the total numbers of calves affected.

TABLE 12

Incidence of Laboratory Confirmed Clinical Joints

| Group | Total Animals Affected | Right Front Fetlock | Knee | Elbow | Shoulder | Left Front Fetlock | Knee | Elbow | Shoulder | Right Rear Fetlock | Hock | Stifle | Hip | Left Rear Fetlock | Hock | Stifle | Hip |
|---|---|---|---|---|---|---|---|---|---|---|---|---|---|---|---|---|---|
| 1 | 6/9 | 0% | 44% | 11% | 0% | 11% | 22% | 0% | 0% | 11% | 11% | 11% | 0% | 33% | 11% | 22% | 0% |
| 2 | 7/9 | 29% | 29% | 0% | 0% | 29% | 86% | 0% | 0% | 29% | 29% | 14% | 14% | 57% | 14% | 14% | 0% |
| 3 | 5/8 | 0% | 38% | 0% | 0% | 0% | 13% | 0% | 0% | 13% | 0% | 13% | 0% | 13% | 13% | 25% | 0% |
| 4 | 6/6 | 50% | 83% | 33% | 0% | 50% | 100% | 0% | 0% | 67% | 17% | 0% | 0% | 83% | 0% | 0% | 0% |
| 5 | 0/2 | 0% | 0% | 0% | 0% | 0% | 0% | 0% | 0% | 0% | 0% | 0% | 0% | 0% | 0% | 0% | 0% |
| 6 | 0/2 | 0% | 0% | 0% | 0% | 0% | 0% | 0% | 0% | 0% | 0% | 0% | 0% | 0% | 0% | 0% | 0% |

Group 1 = Vac I (SQ + IN); 2 = Vac I (SQ only); 3 = Vac I (IN only); 4 = No Vac; 5 = Vac II (SQ + IN); 6 = Vac III (SQ + IN)
Note:
A sample was reported as laboratory confirmed if PCR and/or Culture was positive for *M. bovis*.

PCR Detection of *M. bovis* from Nasal Tonsil and Lung Samples

The nasal passages were sampled from each animal by swab on Day 0, 14, 27, 35 and 41 or Day of Necropsy. In addition, during the post-mortem, samples of tonsils were taken by swab and representative lung tissue was recovered. The following tables show the frequency of detection using real-time PCR targeting a general *M. bovis* marker (uvrC). In addition, tonsil and lung tissue were analyzed using a recently developed end-point PCR assay targeting markers not found in the *M. bovis* challenge isolate but found in all vaccine candidates. As expected, PCR detected the *M. bovis* vaccine and/or the challenge microorganism in various nasal swab samples.

TABLE 13

PCR Detection Frequency of *M. bovis* from Nasal Swab Samples

| Group | n = | D0 | D14 | D27 | D35 | Post |
|---|---|---|---|---|---|---|
| 1 Live Vac I (SQ + IN) | 9 | 0% | 33% | 0% | 11% | 22% |
| 2 Live Vac I (SQ) | 9 | 0% | 0% | 0% | 22% | 0% |
| 3 Live Vac I (IN) | 8 | 0% | 0% | 13% | 0% | 25% |
| 4 No Vac | 6 | 0% | 0% | 0% | 50% | 33% |
| 5 Live Vac II (SQ + IN) | 2 | 0% | 0% | 0% | 50% | 50% |
| 6 Live Vac III (SQ + IN) | 2 | 0% | 0% | 0% | 0% | 100% |

Group 1 = Vac I (SQ + IN); 2 = Vac I (SQ only); 3 = Vac I (IN only); 4 = No Vac; 5 = Vac II (SQ + IN); 6 = Vac III (SQ + IN)
Note:
PCR detection by real-time PCR targeting a general *M. bovis* marker (uvrC).

TABLE 14

PCR Detection Frequency (General *M. bovis* and Non-Challenge assay) from Tonsil and Lung Tissue Samples

| Group | n = | Tonsil General | Tonsil Non-Challenge | Lung General | Lung Non-Challenge |
|---|---|---|---|---|---|
| 1 Live Vac I (SQ + IN) | 9 | 100% | 100% | 67% | 11% |
| 2 Live Vac I (SQ) | 9 | 100% | 0% | 100% | 0% |
| 3 Live Vac I (IN) | 8 | 100% | 100% | 13% | 0% |
| 4 No Vac | 5 | 100% | 0% | 100% | 0% |
| 5 Live Vac II (SQ + IN) | 2 | 100% | 100% | 50% | 0% |
| 6 Live Vac III (SQ + IN) | 2 | 100% | 100% | 50% | 0% |

Group 1 = Vac I (SQ + IN); 2 = Vac I (SQ only); 3 = Vac I (IN only); 4 = No Vac; 5 = Vac II (SQ + IN); 6 = Vac III (SQ + IN)
Note:
General = PCR detection by real-time PCR targeting a general *M. bovis* marker (uvrC);
Non-challenge = PCR detection by end-point PCR targeting markers not found in the *M. bovis* challenge isolate but found in all vaccine candidates.

Again, as expected PCR successfully detected the attenuated live vaccine in tonsil following intranasal vaccination, whereas the challenge microorganism was detected in a high percentage of both lung and tonsil samples.

*M. bovis* Serology

Figure 4:
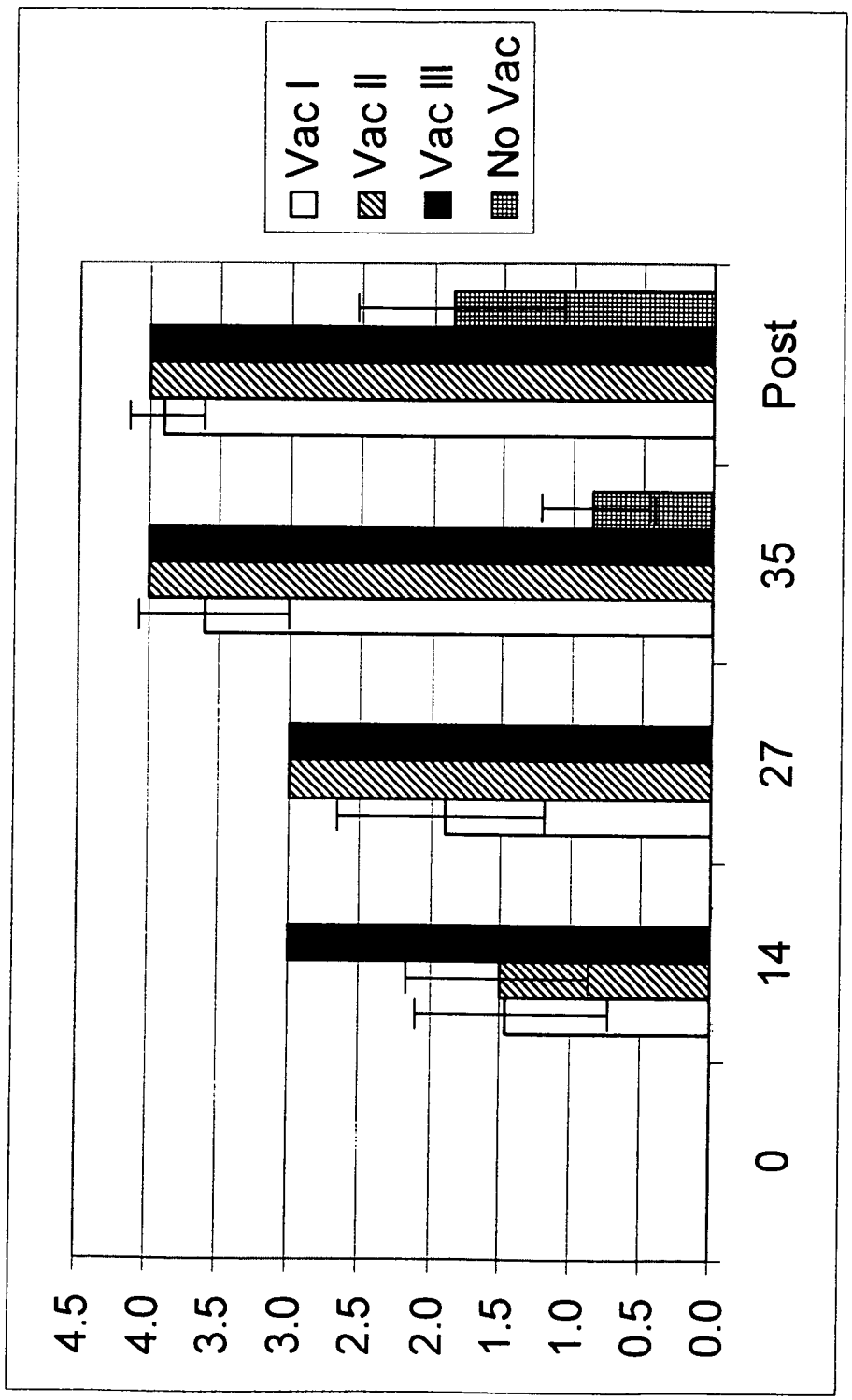
FIG. 4: Comparison of Serology for Live Vac I, TI, III and No Vaccine Group (SQ+IN only)

All samples were tested in the Biovet® *M. bovis* ELISA to monitor the serological response to *M. bovis*. Seroconversion was scored according to grouped multipliers of positivity ODs. The following tables show the mean serological scores detected from each group on Day 0, 14, 27, 35 and Post (post represents a range of study days from 37 to 41 due to early removal of certain animals). The seroconversion seen following vaccination reinforces the conclusion that these new vaccines do provoke a suitable immune response in vaccinated animals such as calves with rapid onset and long duration (see FIG. 4).

Discussion

The objective of this study was to assess the efficacy of three novel and experimental live *Mycoplasma bovis* vaccines including the vaccine (052823A106) (PTA-8694) using various 2 mL administration routes (SQ, IN, SQ+IN) fourteen days apart and a dual challenge model in the target species. The challenge model used administration via the respiratory tract with the additional of a parenteral administration. In addition, two other live vaccine candidates (05249A102 (PTA-8696) and 0519021A106 (PTA-8695) were evaluated for efficacy using only the SQ+IN route.

The challenge and vaccine candidate *Mycoplasma bovis* isolates originated from different naturally infected farms. The procedure using a total volume of 120 mL of the challenge isolate was previously shown when administered to cause both lung pathology and joint disease during experimental challenge and predominated in mixed isolate challenge studies. The live vaccine candidates are high passage isolates originally derived from diagnostic samples. High passage of the vaccine candidates was performed by serial limiting dilution involvement in *Mycoplasma* appropriate media. It is noted that high passage vaccine candidate 052823A106 has demonstrated restricted growth on some *Mycoplasma* selective agar formulations, while the low passage parent isolate has not shown the same characteristic. Additionally, the genotypes of the challenge and vaccine isolates were (as determined by the fingerprinting method) shown to be different.

Multiple parameters were investigated during this study to assess vaccine benefits. Of those parameters, animal removal rates and joint clinical symptoms were used as primary indicators of joint protection. Lung pathology (percent gross lung lesions) was used as the primary indicator of lung protection. Other data such as detection of organism from tissue, joint distribution, and serology provided additional data for confirmation, as did serocoversion to *M. bovis* following vaccination.

Figure 5:
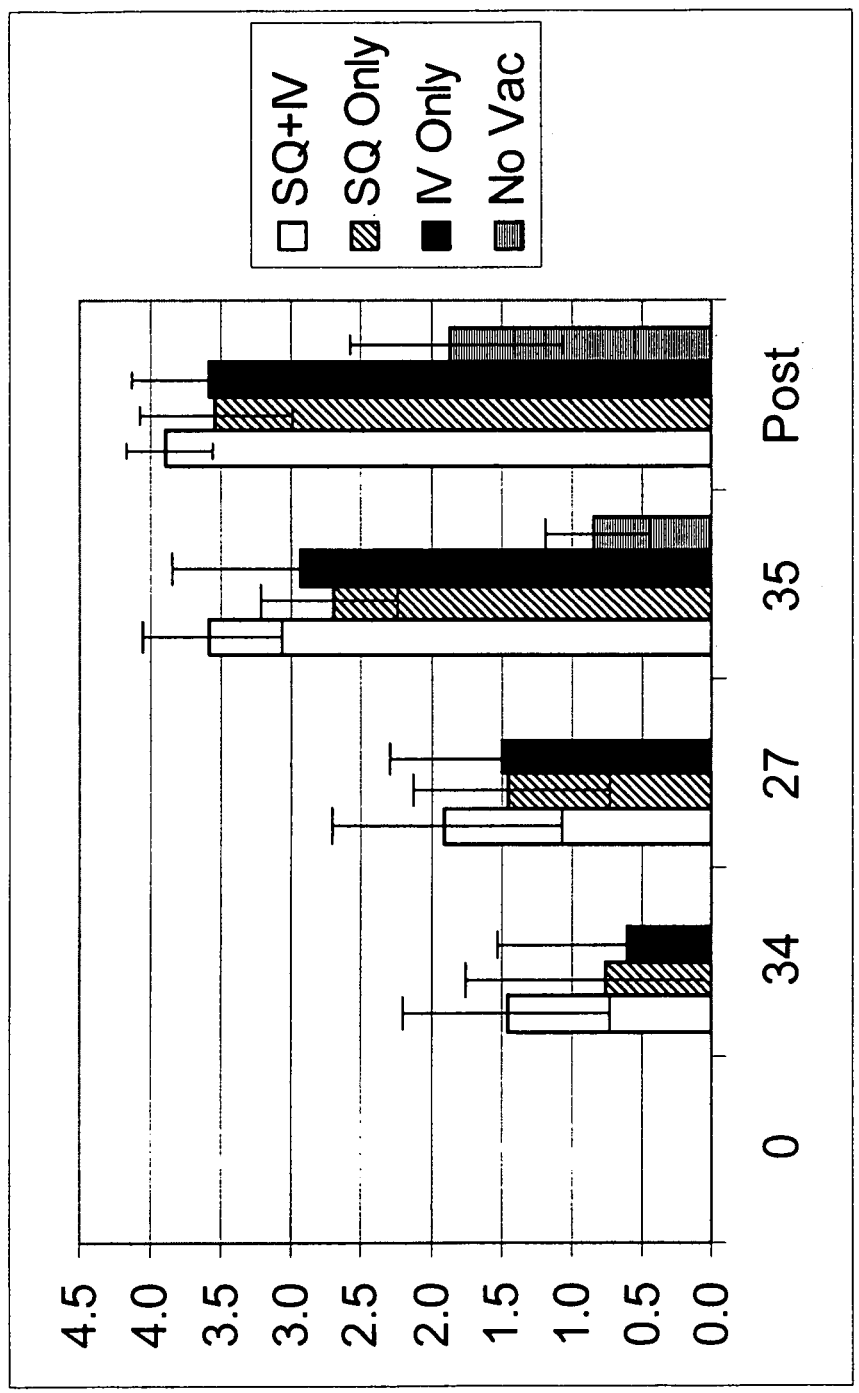
FIG. 5: Comparison of Serology for Live Vac I using Various Routes of Administration

All groups showed disease reducing lung and joint protective benefits after receiving the vaccine candidate *Mycoplasma bovis* Live Vaccine I (052823A106) regardless of route or route combination as demonstrated by a reduction in lung lesions, joint clinical symptoms and animal removal rates. The combined SQ and IN route (Group 1) resulted in the greatest reduction of lung lesions (86%) compared to the groups using only a single route. Additionally, results of lung lesions, joint clinical symptoms and removal rate reductions confirm benefit from receiving the two other vaccine candidates Live Vaccine II (05249A102) and Live Vaccine III (0519021B106) by a combined SQ and IN route. ELISA results demonstrated a strong humoral response to vaccination with all vaccine candidates confirming that the onset of immunity following a single vaccination is as soon as 14 days and that the duration of immunity is at least 41 days (see FIG. 5).

All vaccine candidates demonstrated safety. No animals from any group receiving a vaccine presented with clinical symptoms during the vaccination period and only one animal that had received Live Vaccine III (0519021A106) showed reactivity at an injection site and that reactivity was insignificant. Additionally, results of PCR showed non-challenge *M. bovis* detection from the tonsil tissue of only groups receiving a vaccine candidate via the IN route and detection of non-challenge from lung tissue in only a single animal that had received Live Vaccine I (05-2823 P106) by both IN and SQ routes.

The data support the conclusion that, in general, novel, attenuated live *M. bovis* vaccines made in accordance with the present invention and given by various routes of administration are safe and effective, rapid in onset and long lasting in protection as immunological compositions for vaccination of calves to prevent and reduce various disease manifestations caused by infection with virulent wild type *M. bovis*.

EXAMPLE 3

This example describes the DNA fingerprinting process used to differentiate *M. bovis* strains by isolating, amplifying and detecting DNA using the method and primers as disclosed in WO 2008-030619

Materials and Methods

*Mycoplasma* sp. isolates were used in the studies. Isolates were obtained from in-house sources or field isolates obtained from infected animals. Isolates were grown using a combination of *Mycoplasma*-selective agar and broth for 1-7 days. To isolate DNA, broth cultures were spun and pelleted. DNA from the pellet was then extracted (using the Qiagen DNeasy Tissue Kit and resuspended in molecular grade water). Genomic DNA was quantitated using Picogreen (Invitrogen). Primers were designed based on the known insertion sequences (transposable elements) present in the bacterial genome (*Mycoplasma bovis*) and are disclosed in WO 2008-030619. Outwardly facing primers were manually selected from the element ends (excluding the terminal repeat regions) at a Tm of 55-58 C. PCR reactions were then carried out using a multiplex PCR master mix (Qiagen Multiplex PCR Kit). The reactions contained 1× Master mix, 300 nM of each primer and 1 ng of template DNA. Thermal cycling conditions were 95 C for 15 minutes, 35 cycles of 94 C for 30 seconds, 56.1 C for 90 seconds, 72 C for 2 minutes, with a final extension of 72 C for 4 minutes and a 4 C hold. The amplified products were separated on a 4% agarose gel with ethidium bromide (Invitrogen E-gel), run for 50 minutes at room temperature and imaged under UV light.

Results and Discussion

The results showed that each of the isolates used in this application had a unique fingerprint. However, as shown in Example 2, each isolate was also an effective attenuated live culture vaccine that was effective at providing cross protection against a challenge isolate having a different fingerprint than any of the vaccine candidates. Three field isolates, 052823A106 (PTA-8694), 0549A102 (PTA-8696), and 0519021B106 (PTA-8695), were grown and DNA isolated according to the above protocol. 2-5 ng of DNA from each isolate was amplified according to the above protocol using a multiplex of 4 sets of IS primers identified as SEQ ID Nos. 1-8 as disclosed in WO 2008-030619. The amplified products were separated on a Invitrogen E-gel 4% agarose gel containing ethidium bromide (according to manufacturer) for 50 minutes and visualized under UV light. All isolates produced unique patterns. The patterns were reproducible using independent aliquots under the sample PCR reaction conditions.

The invention claimed is:

1. An attenuated, avirulent *Mycoplasma bovis* bacterium strain, wherein the attenuated, avirulent *Mycoplasma bovis* strain is selected from the group consisting of: the attenuated *Mycoplasma bovis* bacteria strains deposited with the American Type Culture Collection (ATCC) under accession numbers PTA-8694 (052823A106), PTA 8695 (0519021B106), or PTA 8696 (05249A102).

2. An immunogenic composition comprising live bacteria of any of the attenuated, avirulent *Mycoplasma bovis* bacteria strains according to claim 1.

3. The immunogenic composition according to claim 2, further comprising a pharmaceutical acceptable carrier.

4. The immunogenic composition according to claim 2, characterized in that the immunogenic composition comprises at least 10E3 CFU of the live bacteria of the attenuated, avirulent *Mycoplasma bovis* bacteria per dose.

5. The immunogenic composition according to claim 4, characterized in that the immunogenic composition comprises 10E3 to 10E10 CFU of the live bacteria of the attenuated, avirulent *Mycoplasma bovis* bacteria per dose.

6. The immunogenic composition according to claim 2, wherein one dose of the immunogenic composition is formulated in 1 or 2 ml.

7. The immunogenic composition according to claim 2, wherein the immunogenic composition is effective in generating an immune response within 14 days following a single dose administration.

8. The immunogenic composition according to claim 2, wherein the immunogenic composition is effective in a reduction of clinical symptoms following a single dose administration of the immunogenic composition.

9. The immunogenic composition according to claim 2, wherein the immunogenic composition elicits or provokes an immune response when administered to an animal.

10. A method of producing an immunogenic composition, comprising admixing attenuated, avirulent *Mycoplasma bovis* bacterium strain, wherein the attenuated, avirulent *Mycoplasma bovis* strain is selected from the group consisting of: the attenuated *Mycoplasma bovis* bacteria strains deposited with the American Type Culture Collection (ATCC) under accession numbers PTA-8694 (052823A106), PTA 8695 (0519021B106), or PTA 8696 (05249A102),with a pharmaceutical acceptable carrier.

11. An attenuated, avirulent *Mycoplasma bovis* bacterium strain according to claim 1, wherein the bacterium is passaged more than 100 times.

12. An attenuated, avirulent *Mycoplasma bovis* bacterium, strain according to claim 1, wherein the bacterium is passaged more than 102 times.

13. An attenuated, avirulent *Mycoplasma bovis* bacterium, strain according to claim 1, wherein the bacterium is passaged more than 106 times.

14. A method of attenuating avirulent *Mycoplasma bovis* bacterium strain selected from the group consisting of: the attenuated *Mycoplasma bovis* bacteria strains deposited with the American Type Culture Collection (ATCC) under accession numbers PTA-8694 (052823A106), PTA 8695 (0519021B106), or PTA 8696 (05249A102), comprising, a. passaging said Mycoplasma bovis bacteria more than 10 times; b. obtaining the cultured *Mycoplasma bovis* bacteria; c. testing the cultured *Mycoplasma bovis* bacteria obtained under step b) for their pathogenicity and immunogenicity; and d. propagating the non-pathogenic, but immunogenic *Mycoplasma bovis* bacteria to obtain said attenuated *Mycoplasma bovis* bacteria.

15. The method according to claim 14, wherein the *Mycoplasma bovis* bacteria are passaged in vitro.

16. The method according to claim 14, wherein the pathogenicity testing comprises:
   a. infecting cattle with the passaged *Mycoplasma bovis* bacteria; and
   b. monitoring the infected cattle for developing clinical symptoms of a *Mycoplasma bovis* infection.

17. The method according to claim 14, wherein the immunogenic testing comprises:
   a. infecting cattle with the passaged *Mycoplasma bovis* bacteria; and
   b. monitoring the development of the humoral antibody response against *Mycoplasma bovis* in the infected cattle.

18. A method for the treatment of infections caused by *Mycoplasma bovis*, comprising administering an effective amount of attenuated, avirulent *Mycoplasma bovis* bacterium strain, wherein the attenuated, avirulent *Mycoplasma bovis* strain is selected from the group consisting of: the attenuated *Mycoplasma bovis* bacteria strains deposited with the American Type Culture Collection (ATCC) under accession numbers PTA-8694 (052823A106), PTA 8695 (0519021B106), or PTA 8696 (05249A102),to an animal, wherein said treatment is selected from the group consisting of reducing signs of *Mycoplasma bovis* infection, reducing the severity of or incidence of clinical signs of *Mycoplasma bovis* infection, and combinations thereof.

19. The method according to claim 18, wherein only a single dose is administered to said animal.

20. The method according to claim 18, wherein the immunogenic composition is administered to animals from day 1 of age.

21. The method according to claim 18, wherein two doses are administered to said animal.

22. The method according to claim 21, wherein the second dose is administered at least 10 days after the first administration.

23. The method according to claim 18, wherein the animal is cattle.

* * * * *

SEQUENCE LISTING

<160> NUMBER OF SEQ ID NOS: 8

<210> SEQ ID NO 1
<211> LENGTH: 21
<212> TYPE: DNA
<213> ORGANISM: Mycoplasma bovis

<400> SEQUENCE: 1
ccgcaagtta acttgtggtg c                                      21

<210> SEQ ID NO 2
<211> LENGTH: 24
<212> TYPE: DNA
<213> ORGANISM: Mycoplasma bovis

<400> SEQUENCE: 2
ggccattttc ttgtcagaac cacc                                   24

<210> SEQ ID NO 3
<211> LENGTH: 29
<212> TYPE: DNA
<213> ORGANISM: Mycoplasma bovis

<400> SEQUENCE: 3
gcttttactc tggtactaga tggtcttgg                              29

<210> SEQ ID NO 4
<211> LENGTH: 30
<212> TYPE: DNA
<213> ORGANISM: Mycoplasma bovis

<400> SEQUENCE: 4
gtggcgttct tgacaataga acaattagtg                             30

<210> SEQ ID NO 5
<211> LENGTH: 26
<212> TYPE: DNA
<213> ORGANISM: Mycoplasma bovis

<400> SEQUENCE: 5
gatgttcttc attgtctttt gcatcg                                 26

<210> SEQ ID NO 6
<211> LENGTH: 23
<212> TYPE: DNA
<213> ORGANISM: Mycoplasma bovis

<400> SEQUENCE: 6
cgacgagtta caagaaagtt ggc                                    23

<210> SEQ ID NO 7
<211> LENGTH: 29
<212> TYPE: DNA
<213> ORGANISM: Mycoplasma bovis

<400> SEQUENCE: 7
gaaacaccta tcccagtagg tacaagatc                              29

<210> SEQ ID NO 8
<211> LENGTH: 33
<212> TYPE: DNA
<213> ORGANISM: Mycoplasma bovis

```
<400> SEQUENCE: 8
gtctacattg ttcaaaatgc gacattttgt ata                              33
```